US012268716B2

(12) United States Patent
Shimizu

(10) Patent No.: US 12,268,716 B2
(45) Date of Patent: Apr. 8, 2025

(54) COMPOSITION CONTAINING MICROORGANISMS DERIVED FROM LIVING BODY AND METHOD FOR MANUFACTURING THE SAME

(71) Applicant: SHINBIOSIS CORPORATION, Osaka (JP)

(72) Inventor: Shin Shimizu, Osaka (JP)

(73) Assignee: SHINBIOSIS CORPORATION, Osaka (JP)

( * ) Notice: Subject to any disclaimer, the term of this patent is extended or adjusted under 35 U.S.C. 154(b) by 0 days.

(21) Appl. No.: 16/617,691

(22) PCT Filed: Feb. 27, 2019

(86) PCT No.: PCT/JP2019/007574
§ 371 (c)(1),
(2) Date: Nov. 27, 2019

(87) PCT Pub. No.: WO2019/168034
PCT Pub. Date: Sep. 6, 2019

(65) Prior Publication Data
US 2020/0171103 A1 Jun. 4, 2020

(30) Foreign Application Priority Data
Feb. 28, 2018 (JP) ................. 2018-036062

(51) Int. Cl.
| *A61K 35/741* | (2015.01) |
| *A61K 9/00* | (2006.01) |
| *A61K 9/10* | (2006.01) |
| *A61P 1/00* | (2006.01) |
| *B82Y 5/00* | (2011.01) |

(52) U.S. Cl.
CPC .......... *A61K 35/741* (2013.01); *A61K 9/0031* (2013.01); *A61P 1/00* (2018.01); *A61K 9/10* (2013.01); *B82Y 5/00* (2013.01)

(58) Field of Classification Search
CPC . A61K 39/02; A61K 47/6925; A61K 49/0093
USPC ................................................... 424/234.1
See application file for complete search history.

(56) References Cited

U.S. PATENT DOCUMENTS

| 2017/0105935 A1 | 4/2017 | Nakashima et al. | |
| 2020/0061220 A1* | 2/2020 | Exner | A61K 9/1271 |

FOREIGN PATENT DOCUMENTS

| JP | 2007001900 A | 1/2007 | |
| JP | 2007-137791 A | 6/2007 | |
| JP | 2008063246 A | 3/2008 | |
| JP | 2008296095 A * | 12/2008 | |
| JP | 2012-582 A | 1/2012 | |
| JP | 2013119548 A * | 6/2013 | |
| JP | 2013-537531 A | 10/2013 | |
| JP | 2015127301 A * | 7/2015 | A61K 33/00 |
| JP | 2018177714 A | 11/2018 | |
| WO | 2012016287 A2 | 2/2012 | |
| WO | 2016084780 A1 | 6/2016 | |
| WO | 2016/111285 A1 | 7/2016 | |
| WO | 2016133450 A1 | 8/2016 | |
| WO | WO-2016183577 A1 * | 11/2016 | A61K 35/74 |
| WO | 2017125929 A1 | 7/2017 | |
| WO | 2019/057960 A1 | 3/2019 | |

OTHER PUBLICATIONS

International Search Report dated May 28, 2019, issued in counterpart International Application No. PCT/JP2019/007574 (11 pages).
Written Opinion (Form PCT/ISA/237) of the International Searching Authority dated May 28, 2019, issued in counterpart International Application No. PCT/JP2019/007574 (7 pages).
Nood, E. et al.; "Duodenal Infusion of Donor Feces for Recurrent Clostridium difficile", The new England journal of medicine, Jan. 31, 2013, vol. 368. No.5, pp. 407-415 (9 pages), cited in specification.
Els Van Nood et al: "Duodenal Infusion of Donor Feces for Recurrent Clostridium difficile", New England Journal of Medicine, vol. 368, No. 5, Jan. 31, 2013 (Jan. 31, 2013), pp. 407-415, XP055095085; Cited in Extended European Search Report dated Oct. 29, 2021. (9 pages).
Walter Jens et al: "To engraft or not to engraft: an ecological framework for gut microbiome modulation with live microbes", Current Opinion in Biotechnology, vol. 49, Feb. 1, 2018 (Feb. 1, 2018), pp. 129-139, XP055848363; Cited in Extended European Search Report dated Oct. 29, 2021. (11 pages).
The Extended European Search Report dated Oct. 29, 2021, issued in counterpart EP Application No. 19761166.8. (11 pages).
Office Action dated Mar. 29, 2022, issued in counterpart JP Application No. 2020-503570, with English Translation. (10 pages).
Office Action dated May 24, 2022, issued in counterpart JP Application No. 2020-503570, with English Translation. (6 pages).
First Office Action for CN Application No. 201980002823.9 dated Oct. 10, 2022 with EN Translation.
Second Office Action for CN Application No. 201980002823.9 dated Jun. 1, 2023 with EN Translation.
Third Office Action for CN Application No. 201980002823.9 dated Oct. 31, 2023 with EN Translation.
First Office Action for KR Application No. KR 10-2019-7033115 dated Dec. 9, 2020 with EN Translation.
First Office Action for KR Divisional Application No. KR 10-2023-7010602 dated Jun. 2, 2023 with EN Translation.

(Continued)

*Primary Examiner* — Jana A Hines
*Assistant Examiner* — Khatol S Shahnan Shah
(74) *Attorney, Agent, or Firm* — Calfee, Halter & Griswold LLP

(57) ABSTRACT

Provided is a composition containing microorganisms derived from a living body with which more rapid and more reliable engraftment effect is achieved irrespective of the administration method and the administration route.
A composition containing microorganisms derived from a living body, comprising (I) to (III) below is provided.
(I) At least one or more types of microorganisms.
(II) A solvent.
(III) Nano-sized or smaller gas bubbles.

9 Claims, 10 Drawing Sheets

(56) References Cited

OTHER PUBLICATIONS

Li, Xiongbiao, "Clostridium butyricum: the Guardian of Intestinal Health" Fudan University Press, pp. 24-25 dated Jan. 31, 2008 with partial EN Translation.
China National Intellectual Property Administration (CNIPA), Rejection Decision for CN Application No. 201980002823.9 dated Mar. 1, 2024 with EN Translation.
European Patent Office, Communication Pursuant to Article 94(3) EPC (Office Action) for EP Application No. 19761166.8, dated Jun. 6, 2024, pp. 1-6.
Anonymous, "Differences From Other Fecal Microbiota Transplants." The Association for Clinical Research of Fecal Microbiota Transplantation, Japan, Dec. 14, 2017. https://fmt-japan.org/en/technical-features/.

\* cited by examiner

FIG. 10A

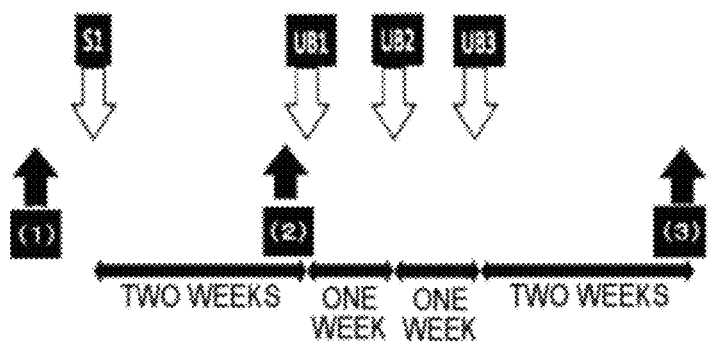

S1: TRANSPLANTATION OF CONVENTIONAL COMPOSITION CONTAINING MICROORGANISMS FROM LIVING BODY FIRST TIME
UB1: TRANSPLANTATION OF COMPOSITION CONTAINING MICROORGANISMS FROM LIVING BODY OF THE PRESENT INVENTION FIRST TIME
UB2: TRANSPLANTATION OF COMPOSITION CONTAINING MICROORGANISMS FROM LIVING BODY OF THE PRESENT INVENTION SECOND TIME
UB3: TRANSPLANTATION OF COMPOSITION CONTAINING MICROORGANISMS FROM LIVING BODY OF THE PRESENT INVENTION THIRD TIME (1) COLLECTION OF FECES BEFORE TRANSPLANTATION OF MICROORGANISMS DERIVED FROM LIVING BODY
(2) COLLECTION OF FECES TWO WEEKS AFTER IMPLEMENTATION OF S1
(3) COLLECTION OF FECES TWO WEEKS AFTER IMPLEMENTATION OF UB3

FIG. 11A

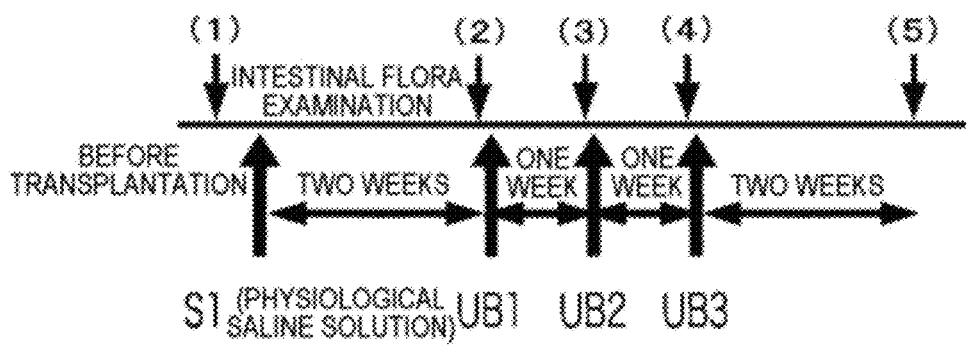

S1: TRANSPLANTATION OF CONVENTIONAL COMPOSITION CONTAINING MICROORGANISMS FROM LIVING BODY FIRST TIME
UB1: TRANSPLANTATION OF COMPOSITION CONTAINING MICROORGANISMS FROM LIVING BODY OF THE PRESENT INVENTION FIRST TIME
UB2: TRANSPLANTATION OF COMPOSITION CONTAINING MICROORGANISMS FROM LIVING BODY OF THE PRESENT INVENTION SECOND TIME
UB3: TRANSPLANTATION OF COMPOSITION CONTAINING MICROORGANISMS FROM LIVING BODY OF THE PRESENT INVENTION THIRD TIME (1) COLLECTION OF FECES BEFORE TRANSPLANTATION OF MICROORGANISMS DERIVED FROM LIVING BODY
(2) COLLECTION OF FECES TWO WEEKS AFTER IMPLEMENTATION OF S1
(3) COLLECTION OF FECES ONE WEEK AFTER IMPLEMENTATION OF UB1
(4) COLLECTION OF FECES ONE WEEK AFTER IMPLEMENTATION OF UB2
(5) COLLECTION OF FECES TWO WEEKS AFTER IMPLEMENTATION OF UB3

COMPOSITION CONTAINING MICROORGANISMS DERIVED FROM LIVING BODY AND METHOD FOR MANUFACTURING THE SAME

TECHNICAL FIELD

The present invention relates to a composition containing microorganisms derived from a living body and minute gas bubbles, a method for manufacturing the same, and the like.

BACKGROUND ART

In recent years, functions of microorganisms that are present in living bodies have been attracting attention. In particular, the importance of the balance of "intestinal flora" has been pointed out.

The term "intestinal flora" is derived from the fact that a state in which intestinal microorganisms that are of the same kind or have the same characteristics gather in some degree and live on the intestinal wall seems like a flower garden in which flowers of the same type bloom in clusters.

"The kinds of or the ratio between the kinds of" microorganisms in the "intestinal flora" is called the "intestinal flora balance", and this varies for different kinds of organisms or different individuals. However, as it has been said particularly that "all diseases begin in the intestines", it has been revealed that the tendency of the "intestinal flora balance" of an organism that suffers from some kind of disease or is in a poor physical condition is different from the tendency of those of healthy organisms of the same kind (e.g., humans in the case where the above-mentioned organism is a human).

Typical examples of a method for improving the "intestinal flora balance" include, for example, ingestion of a lactic acid bacteria beverage etc., but it is difficult to produce a dramatic improvement by using only such a method.

To address this, around 2013, a study group in the Netherlands used a revolutionary method (intestinal flora transplantation) in which "intestinal flora itself derived from a healthy individual is directly transplanted into the intestines of a patient" (Non-Patent Document 1), and the efficacy of this method has attracted attention. As a result, nowadays, many projects that aim to treat various diseases are underway both domestically and internationally (Non-Patent Document 2).

This "intestinal flora transplantation" specifically means "fecal (feces-derived) microbiota transplantation (FMT)", which is a technique in which a composition containing intestinal microorganisms is obtained by dissolving feces in a solvent such as a physiological saline solution and is then transplanted to another individual.

However, it is said that conventional "intestinal flora transplantation" techniques have various problems requiring improvement.

First, with conventional methods, it is thought to take several days for the transplanted microorganisms derived from a living body to colonize in a live state (referred to as "engraft" hereinafter) in another living body.

Accordingly it is possible that most of the transplanted "intestinal flora" is excreted from the body of a patient in those several days, and as a result, this is one cause of no retention of the transplanted "intestinal flora" in the body of a patient.

Second, most conventionally used administration methods employ a large intestine endoscope technique (colonoscopy), and thus a heavy burden is placed on a patient.

Third, there is the biggest problem in which it is reported that the colonization ratio (referred to as "engraftment ratio" hereinafter) of the microorganisms derived from a living body after transplantation is no more than 20% to 30% regardless of making various attempts, and as a result, the effect on the treatment of diseases, which is the final goal, is not as great as expected.

On the other hand, apparatuses for generating minute gas bubbles having a diameter of several tens of µm or less, that is, what is called microbubbles, or nanobubbles having a diameter smaller than 1 µm have been developed (Patent Document 1, etc.), and solutions containing such gas bubbles have come into use in various fields such as the medical field, the agricultural field, the fishery field, the aquacultural field, and the like.

However, unlike the present invention, there has been no technical idea of using a solution containing minute gas bubbles (i.e., nanobubble water) to cause bacteria to engraft in a living body in a live state.

CITATION LIST

Patent Document

Patent Document 1: JP 2012-582A

Non-Patent Documents

Non-Patent Document 1: Duodenal Infusion of Donor Feces for Recurrent *Clostridium difficile* (Els van Nood, et al, The new England journal of medicine, Jan. 31, 2013, vol. 368, no. 5, P. 407-415)

Non-Patent Document 2: The latest trend in fecal microbiota transplantation for inflammatory bowel disease. (Modern Media, vol. 62, no. 3, 2016 (Intestinal Bacterial Flora), P. 69-74)

SUMMARY OF INVENTION

Technical Problem

Surprisingly the inventor of the present invention found that, due to a solvent containing microorganisms derived from a living body together with minute gas bubbles, intestinal bacteria easily engrafted in a living body without being inhibited by the mucous membrane of the intestinal wall, which includes mucopolysaccharides etc., and that the engraftment speed and the engraftment ratio significantly increased compared with a case where a conventional method is used, and the present invention was thus accomplished. It is an object of the present invention to provide a "composition containing microorganisms derived from a living body" that has an excellent effect on engraftment in a living body, particularly an excellent effect on engraftment in a living body via the mucous membrane of the intestinal tract or the like, a "composition for adjusting the balance of resident microorganisms" using the same, and the like.

Solution to Problem

The above-described object is achieved by the following first to sixteenth aspects of the present invention.

First Aspect

A composition containing microorganisms derived from a living body, including (I) to (III) below:
(I) at least one or more kinds of microorganisms;
(II) a solvent; and
(III) nano-sized or smaller (smaller than 1 μm) gas bubbles.

Second Aspect

The composition according to the first aspect,
wherein a gas component in the gas bubbles is constituted by one or more kinds of gasses listed below:
(i) air;
(ii) hydrogen;
(iii) nitrogen;
(iv) ozone;
(v) oxygen;
(vi) carbon dioxide; and
(vii) argon.

Third Aspect

The composition according to the first or second aspect, wherein intestinal bacteria are used as (I).

Fourth Aspect

The composition according to any one of the first to third aspects, wherein microorganisms derived from a living body collected from one or more individuals that may or may not include an administration target are used as (I).

Fifth Aspect

A composition for adjusting balance of resident microorganisms, including the composition according to any one of the first to fourth aspects.

Sixth Aspect

The composition according to the fifth aspect, wherein the balance of resident microorganisms is intestinal flora balance.

Seventh Aspect

The composition according to any one of the first to sixth aspects, wherein an administration route is that via an oral cavity eyes, ears, a nose, a vagina, a urethra, a skin, and an anus.

Eighth Aspect

The composition according to any one of the first to seventh aspects, for engraftment via a mucous membrane.

Ninth Aspect

A method for manufacturing the composition according to any one of the first to eighth aspects, including at least steps of (1) and (2) below:
(1) a step of generating gas bubbles of (III) in a solvent (II); and
(2) a step of dispersing and or dissolving (I) in (II),
where (I) to (III) are as follows:
(I) at least one or more kinds of microorganisms derived from a living body;
(II) a solvent; and
(III) nano-sized or smaller gas bubbles.

Tenth Aspect

The manufacturing method according to the ninth aspect, further including a step of (3) below:
(3) a step of determining the kinds of and the ratio between the kinds of microorganisms derived from a living body in (I), and/or one or more individuals from which (I) is collected, depending on an attribute and/or environment of an administration target.

Eleventh Aspect

A method for determining a constitution of the composition according to any one of the first to eighth aspects, including steps below:
(A) a step of estimating the kind of "balance of microorganisms derived from a living body" to be administered; and
(B) a step of selecting "microorganisms derived from a living body" collected from one or more individuals that may or may not include an administration target, such that the "kind of the balance of microorganisms derived from a living body" estimated in (A) can be achieved by them.

Twelfth Aspect

An instrument for administering the composition according to any one of the first to eighth aspects, including a tubular portion, the instrument being an instrument for administration via an anus.

Thirteenth Aspect

An assistant solvent for introduction into a living body, including (II) and (III) below:
(II) a solvent; and
(III) nano-sized or smaller gas bubbles.

Fourteenth Aspect

An agent for improving a physical constitution and/or physical condition, including the composition according to any one of the first to eighth aspects.

Fifteenth Aspect

A method for preventing and/or treating a disease, or improving a physical constitution and/or physical condition, wherein the composition according to any one of the first to eighth aspects is introduced into a living body.

Sixteenth Aspect

A method for introducing an objective substance into a living body by using the assistant solvent for introduction into a living body according to the thirteenth aspect.

Advantageous Effects of Invention

The composition of the present invention can also be administered using a simple method that is less burdensome on a patient compared with a conventional method, and a more rapid and more reliable engraftment effect is achieved irrespective of the administration method and the administration route.

BRIEF DESCRIPTION OF DRAWINGS

FIG. 10A is a diagram showing a procedure to administer a composition of the present invention (intestinal flora derived from "donors") to a "recipient" (patient suffering from giardiasis).

FIG. 11A is a diagram showing a procedure to administer a composition of the present invention (intestinal flora derived from "donors") to a "recipient" (patient suffering from chronic fatigue syndrome).

DESCRIPTION OF EMBODIMENTS

Figure 1:
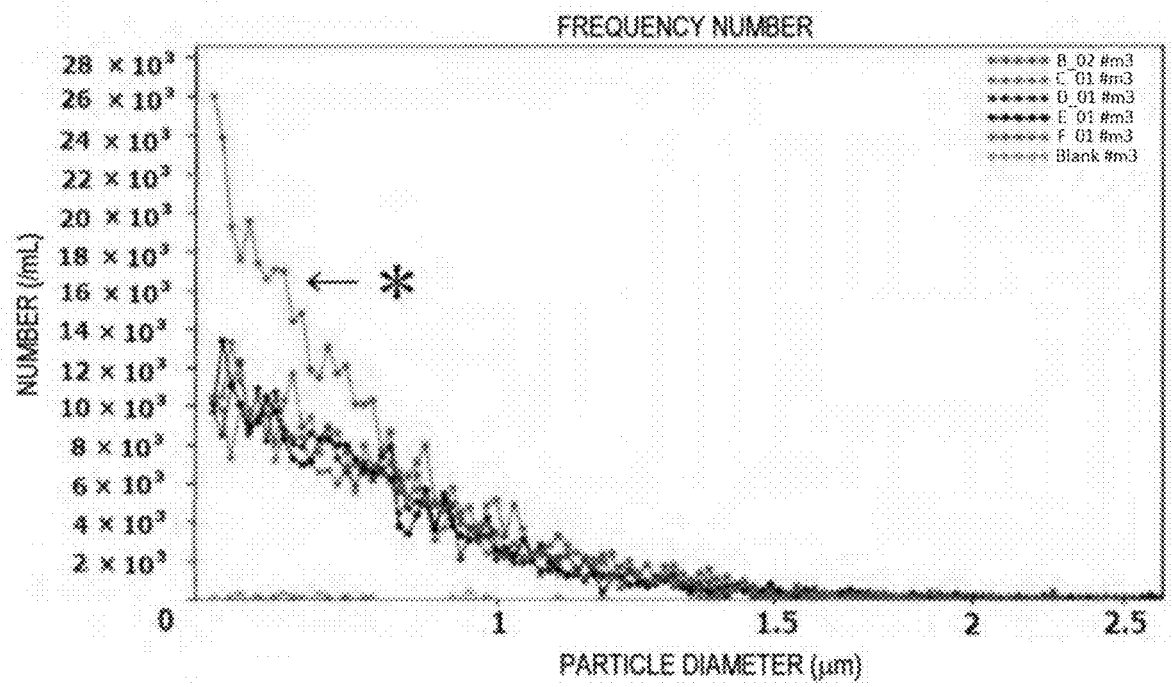
FIG. 1 shows the results from the measurements of the size, number, and the like of gas bubbles in an "assistant solvent for introduction into a living body (nanobubble water A)" (250-fold diluted solution for a measurement) of Example A used in the present invention.
Figure 2:
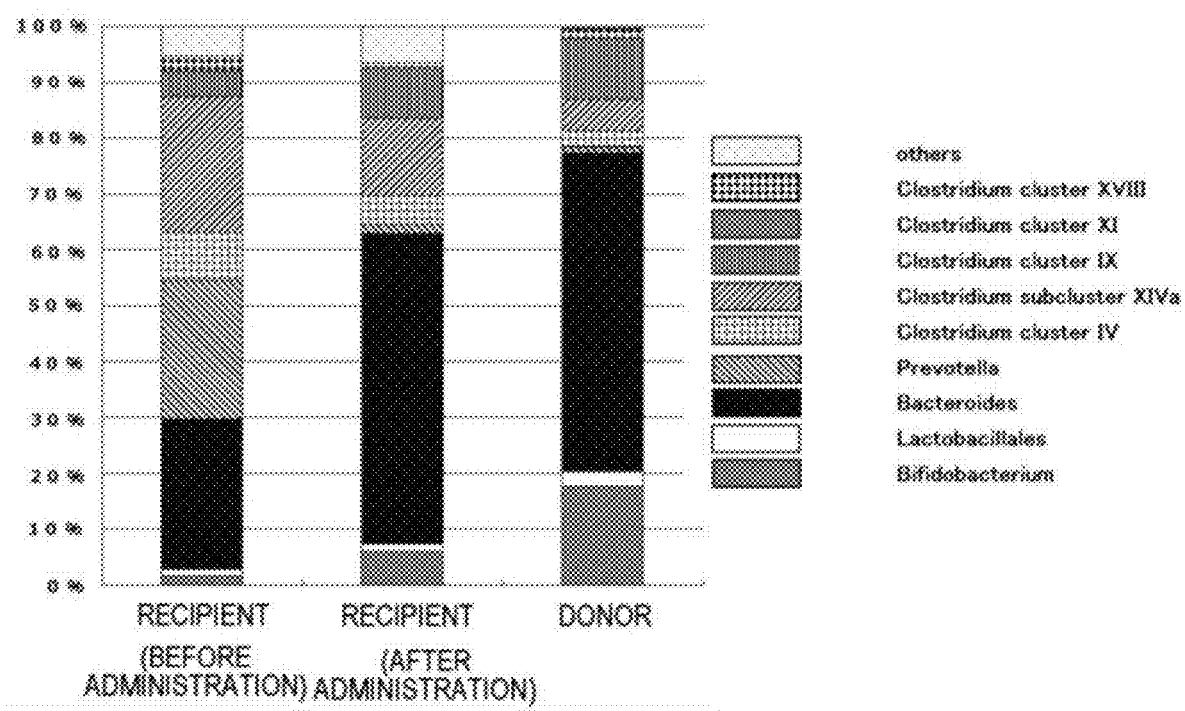
FIG. 2 is a diagram showing a change in the intestinal flora of a "recipient" (patient suffering from atopic dermatitis) when administering a composition of Example 2 (intestinal flora derived from a "donor").
Figure 3:
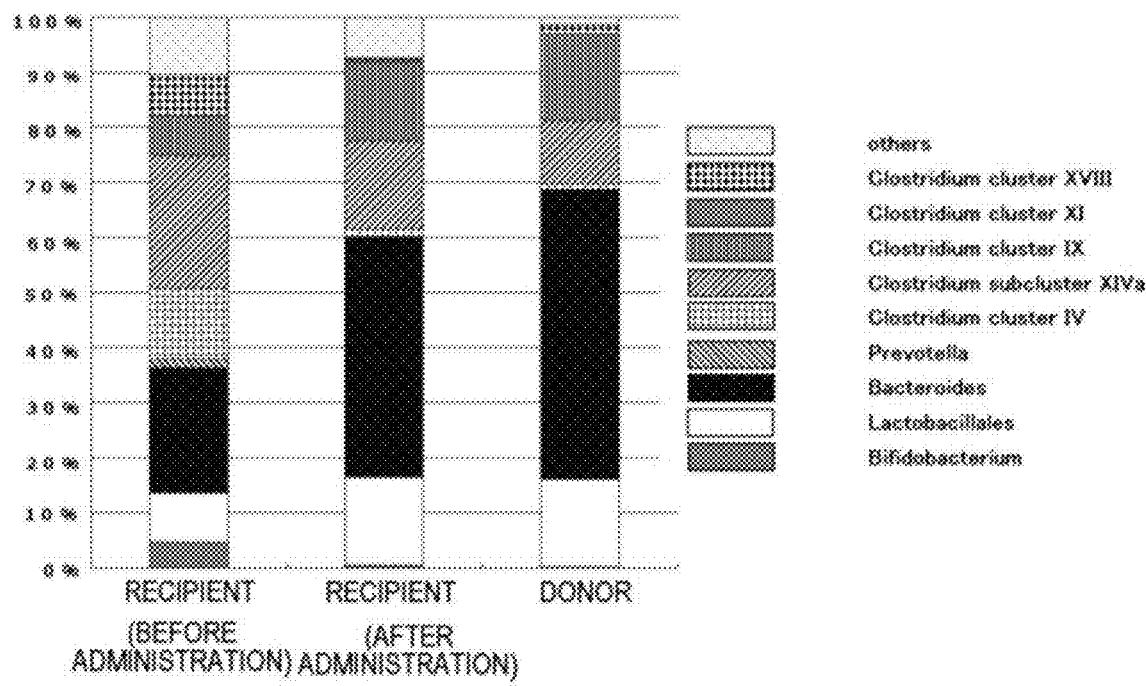
FIG. 3 is a diagram showing a change in the intestinal flora of a "recipient" (patient suffering from pulmonary adenocarcinoma) when administering a composition of Example 3 (intestinal flora derived from a "donor").
Figure 4:
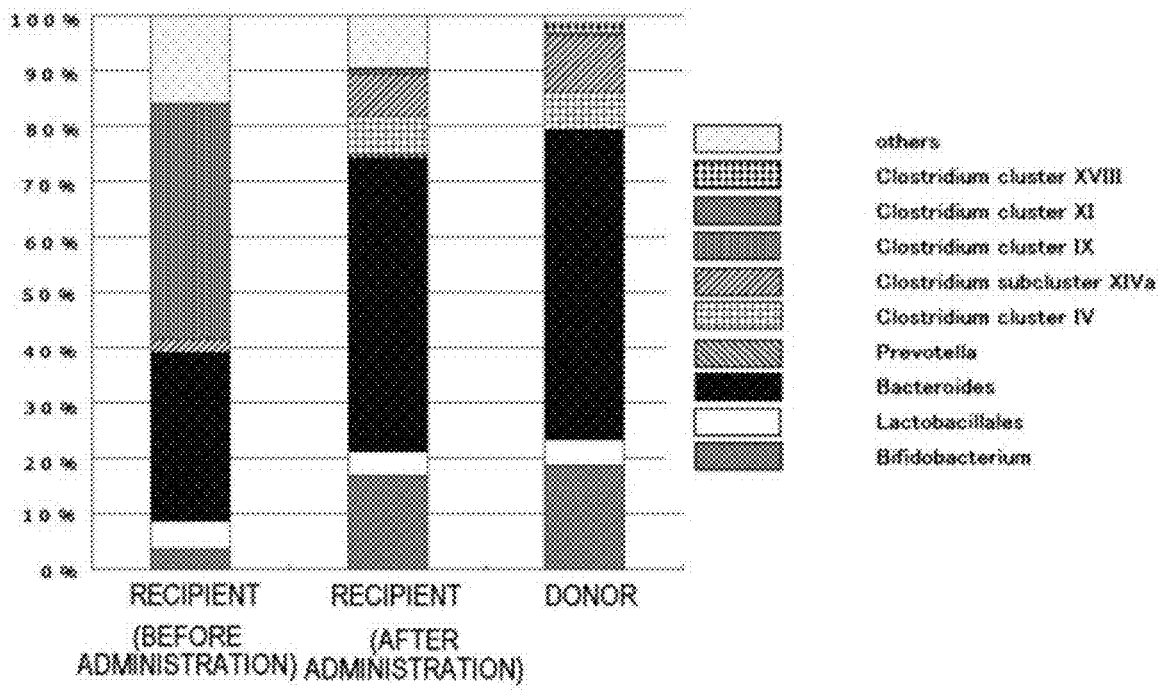
FIG. 4 is a diagram showing a change in the intestinal flora of a "recipient" (patient suffering from chronic pancreatitis) when administering a composition of Example 4 (intestinal flora derived from a "donor").
Figure 5:
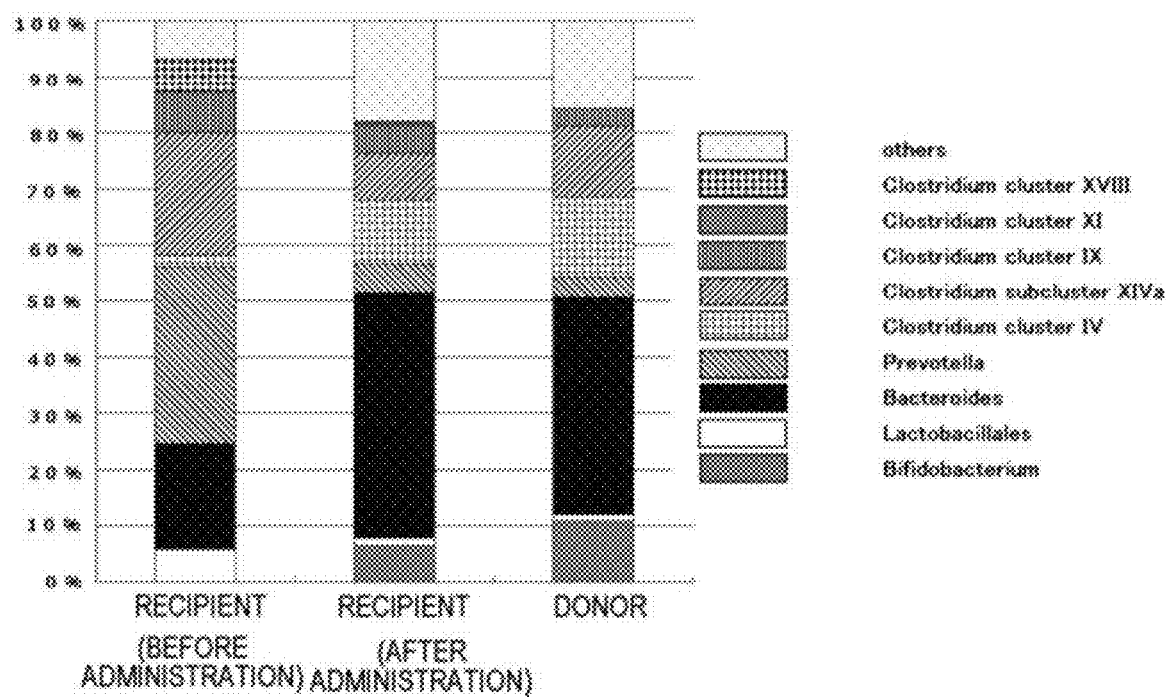
FIG. 5 is a diagram showing a change in the intestinal flora of a "recipient" (patient suffering from type 2 diabetes) when administering a composition of Example 5 (intestinal flora derived from a "donor").
Figure 6:
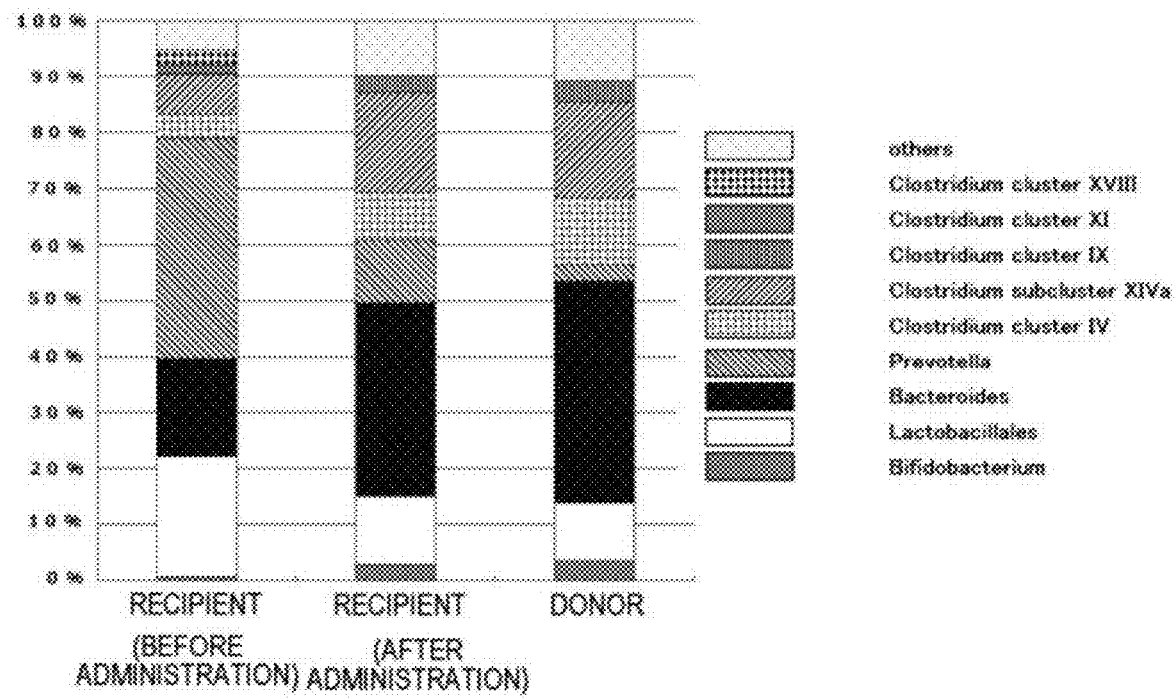
FIG. 6 is a diagram showing a change in the intestinal flora of a "recipient" (patient suffering from diabetic dyslipidemia) when administering a composition of Example 6 (intestinal flora derived from a "donor").
Figure 7:
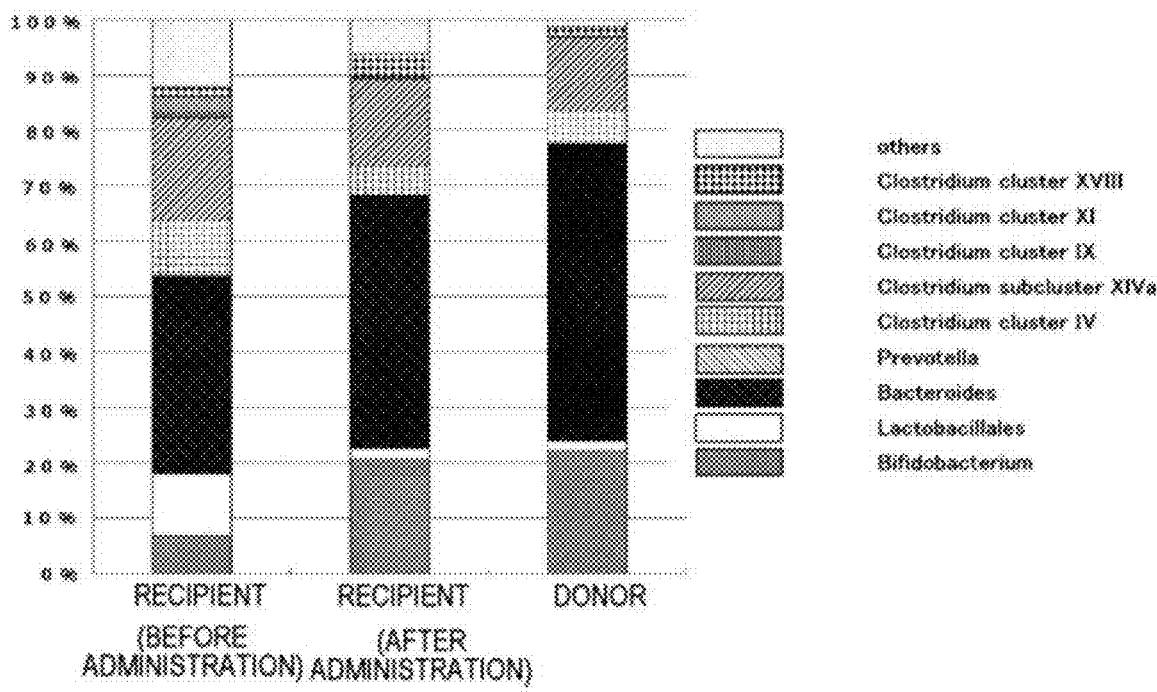
FIG. 7 is a diagram showing a change in the intestinal flora of a "recipient" (patient suffering from irritable bowel syndrome) when administering a composition of Example 7 (intestinal flora derived from a "donor").
Figure 8:
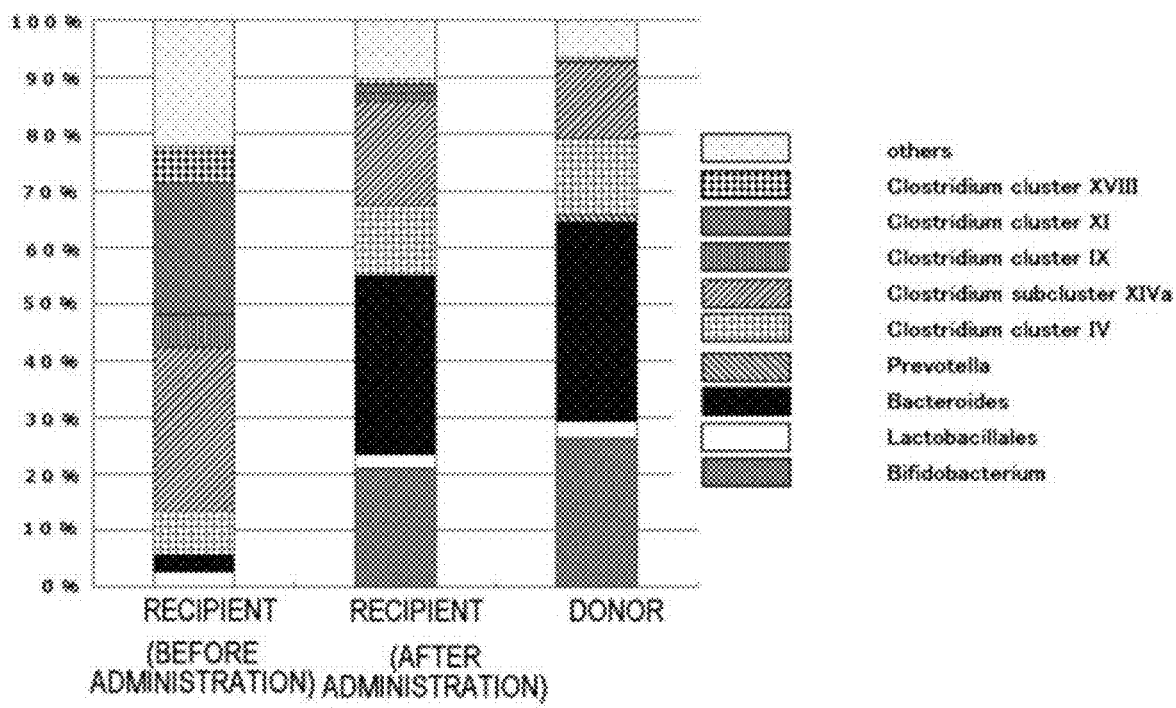
FIG. 8 is a diagram showing a change in the intestinal flora of a "recipient" (patient suffering from ulcerative colitis) when administering a composition of Example 8 (intestinal flora derived from a "donor").
Figure 9:
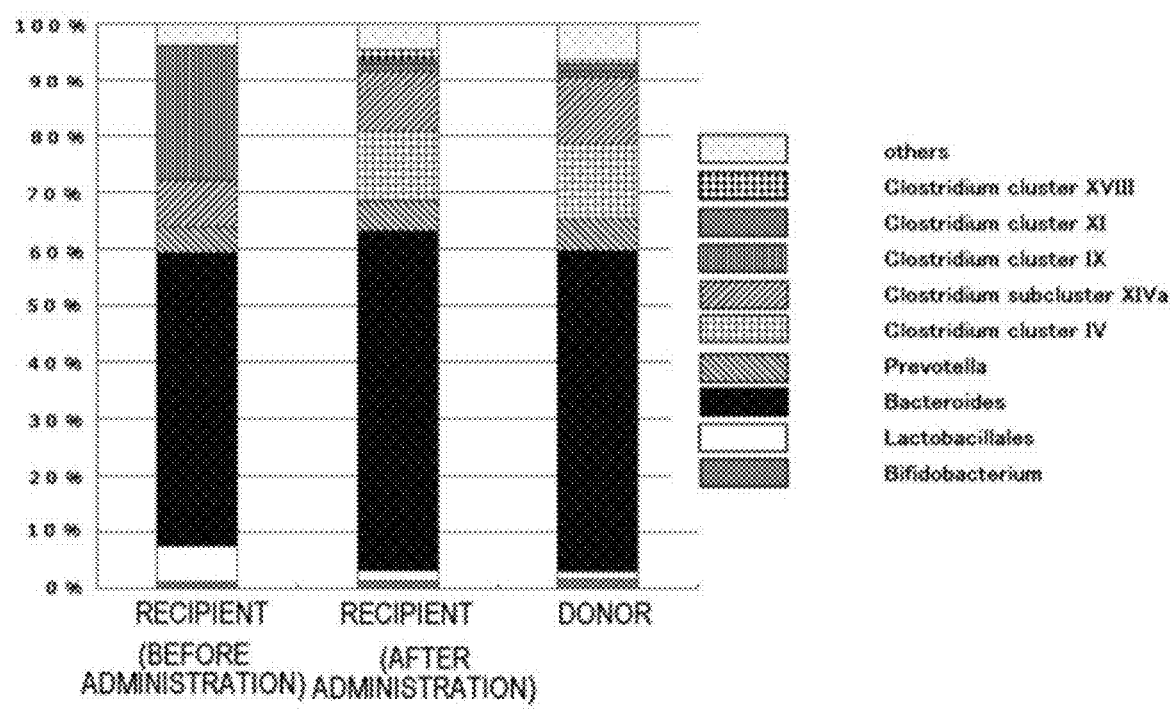
FIG. 9 is a diagram showing a change in the intestinal flora of a "recipient" (patient suffering from depression) when administering a composition of Example 9 (intestinal flora derived from a "donor").

Hereinafter, the present invention will be described in detail.

Composition Containing Microorganisms Derived from Living Body According to the Present Invention A "composition containing microorganisms derived from a living body" of the present invention includes (I) to (III) below:

(I) at least one or more kinds of microorganisms;
(II) a solvent; and
(III) nano-sized or smaller gas bubbles.

Microorganisms Derived from Living Body of (I) Used in the Present Invention

Broad Classification of Microorganisms Derived from Living Body

Microorganisms derived from a living body of (I) used in the present invention refer to all the microorganisms that normally live in every portion of a living body, including the inside of the body, the body surface, and the like of humans and other organisms, and are classified, for example, into bacteria, fungi, viruses, and the like, (the expressions "microorganisms isolated from a living body", "resident microorganisms", "gastrointestinal microorganisms (as a concrete example)", "resident/gastrointestinal (as a concrete example) microorganisms which reside in a living body such as human", and the like may also be used).

These microorganisms derived from a living body encompass not only microorganisms that are directly collected from a living body, but also microorganisms obtained by artificially proliferating those microorganisms, mutants of those microorganisms, artificially modified microorganisms obtained through a transformation technique or other techniques, and the like.

Intermediate Classification of Microorganisms Derived from Living Body

The above-mentioned broad classification groups of the microorganisms derived from a living body include the intermediate classification groups described below.

Intermediate Classification of Bacteria

Specific examples of intermediate classification groups of the bacteria include bacteria that normally live in the intestines, the eyes, the nose and ears, the oral cavity, the vagina, the respiratory tract, the skin, and the like.

Intermediate Classification of Fungi

Examples of intermediate classification groups of the fungi include yeast-like fungi, candida, and yeast.

Intermediate Classification of Viruses

Examples of intermediate classification groups of the viruses include DNA viruses and RNA viruses such as herpesviruses, adenoviruses, smallpox viruses, EB viruses, and mumps viruses.

It should be noted that, when the composition of the present invention is a "composition for adjusting intestinal flora balance", the microorganisms derived from a living body of (I) are preferably intestinal microorganisms or more preferably intestinal bacteria (which may also be expressed as "enteric bacteria", "gastrointestinal bacteria", or the like).

Specific Classification of Intestinal Bacteria

Specific examples of the specific classification groups of the intestinal bacteria include the following groups:

*Bifidobacterium;*
*Lactobacillales;*
*Bacteroides;*
*Prevotella;*
*Clostridium* cluster IV;
*Clostridium* subcluster XIVa;
*Clostridium* cluster IX;
*Clostridium* cluster XI;
*Clostridium* cluster XVIII; and
other *Clostridium.*

It is preferable that the intestinal bacteria are intestinal bacteria derived from the same species (e.g., human in the case where the target is a human).

Number of Intermediate Classification Groups and Specific Classification Groups to be Used Commonly it is preferable to use one of the above-mentioned "intermediate classification groups" as the "microorganisms derived from a living body (I)" to be used in the "composition containing microorganisms derived from a living body" of the present invention, but it may also be preferable to use two or more of the "intermediate classification groups".

Moreover, one or two or more of the "specific classification groups" of the intermediate classification groups can be selected and used as appropriate depending on the "attribute and/or environment" of the administration target (also referred to as "recipient" hereinafter), which will be described later, or other conditions.

For example, when the "composition containing microorganisms derived from a living body" of the present invention is used in a "composition for adjusting the balance of resident microorganisms", which will be described later, it is preferable that (I) is a mixture of two or more kinds of microorganisms derived from a living body. In particular, when the "microorganisms derived from a living body (I)" are "intestinal microorganisms", it is preferable to use two or more kinds of intestinal microorganisms or the entire "intestinal flora" derived from a healthy human.

If it is clear that the shortage of a specific intestinal microorganism causes some kind of disease, it may be sufficient that only that microbial species is administered. However, the causation between a disease and a specific intestinal microorganism is not so clear in many cases at this time. In such a case, it is thought that the transplantation of multiple kinds of intestinal microorganisms or the entire "intestinal flora" derived from a healthy human is an easier way to treat the disease than the administration of that specific intestinal microorganism.

Origin of Microorganisms Derived from Living Body

As the "microorganisms derived from a living body (I)" to be used in the "composition containing microorganisms derived from a living body" of the present invention, those derived from an individual that is the same as an administration target or different therefrom can be used.

The term "(individual that is) the same as an administration target" refers to the administration target (recipient) itself.

It should be noted that, in order to collect "microorganisms derived from a living body (I)" having "activity or an in-vivo balance that is desirable for the composition of the present invention", microorganisms derived from an individual that is different from an administration target, particularly a healthy animal (preferably a human) (that at least does not suffer from the same disease or the like as the administration target suffers from), are preferable.

Mixture of Microorganisms Derived from Living Body

It may be preferable to mix microorganisms derived from two or more individuals and use the mixture as the "microorganisms derived from a living body (I)" to be used in the "composition containing microorganisms derived from a living body" of the present invention.

The reason for this is that even microorganisms belonging to the same classification differ in terms of the growth activity of the microorganisms, the amounts of produced enzymes, and other activities, depending on the sources, and using microorganisms derived from two or more individuals increases the possibility that the microorganisms more reliably engraft in an administration target and become useful for treatment of the administration target, and the like.

Kinds of and Ratio Between Kinds of Microorganisms Derived from Living Body

When multiple kinds of "microorganisms derived from a living body" of (I) are used, it is preferable to individually determine the "kinds" and "ratio between the kinds" thereof based on a comparison in which the "kinds" of and "ratio between the kinds" of "resident microorganisms" (i.e., balance of resident microorganisms) that are originally contained in a target (an animal including a human) (recipient) to which the "composition containing microorganisms derived from a living body" of the present invention is to be administered are compared with the "balance of resident microorganisms" of a healthy individual that is different from the "recipient".

Moreover, it is preferable to carefully determine the "kinds" of and "ratio between the kinds" of the "microorganisms from a living body" by taking into account the above-described comparison as well as the "attribute and/or environment" of the "recipient" as described in step (3) of the section "Method For Manufacturing Composition Of The Present Invention", which will be described later, and the like, the findings and experiences that have been accumulated in the technical field of "transplantation of microorganisms derived from a living body", and the like.

It may be preferable to use, as (I) for actual use, the entirety of microorganisms derived from a living body that are collected from, for example, one or more healthy individuals (preferably humans; also referred to as "donors" hereinafter) that are different from the "recipient", as they are, without making selection of bacteria, or the like.

The reason for this is that microorganisms can be transplanted to the "recipient" while keeping the balance of the resident microorganisms of an individual that has already been confirmed to be healthy, and it is possible to also simultaneously administer various microorganisms contained in resident microorganisms of the healthy individual other than main microorganisms thereof that were deliberately selected in expectation of a treatment effect.

It is quite possible that such other various microorganisms also contribute to the maintenance of health of the "donor".

Content Ratio of Microorganisms Derived from Living Body (I) in Composition

The concentration (content ratio) of the "microorganisms derived from a living body (I)" in the "composition containing microorganisms derived from a living body" of the present invention depends on the "attribute and/or environment" of a "recipient", which will be described later, the administration method, the administration frequency the administration period, and the like, and is thus determined as appropriate.

Method for Preparing Microorganisms Derived from Living Body

There is no particular limitation on the method for preparing the "microorganisms derived from a living body (I)" to be used in the "composition containing microorganisms derived from a living body" of the present invention, but from the viewpoint of "ensuring the repeatability of the balance of resident microorganisms in a healthy condition", "convenience of preparation", and the like, it is preferable to use "microorganisms derived from a living body (I)" prepared by processing a "biological sample" (e.g., feces in a case where the microorganisms derived from a living body are intestinal bacteria) derived from a healthy "donor" using the following method. In particular, it is preferable that the biological sample is derived from a healthy human.

Method for Processing Biological Sample

In order to prepare, from a biological sample, the "microorganisms derived from a living body (I)" to be used in the "composition containing microorganisms derived from a living body" of the present invention, the following describes an example of a method for filtering and purifying the biological sample.

A biological sample is immersed in a biological sample processing solution and partially dissolved, for example, under slight stirring, and then naturally dissolved completely, and then impurities such as food residue are filtered out by performing filtration multiple times using sterilized gauze.

It should be noted that there is no particular limitation on the biological sample processing solution as long as the "microorganisms derived from a living body (I)" to be used in the "composition containing microorganisms derived from a living body" of the present invention are not inactivated, and examples thereof include pure water (purified water) and a physiological saline solution.

There is no problem if this biological sample processing solution is used to process a biological sample and then is replaced with a "solvent (II)", which will be described later again. However, it is preferable to use, in this step, the "solvent (II)" to be used in the "composition containing microorganisms derived from a living body" of the present invention in order to avoid the risk of inactivation of the microorganisms derived from a living body and the like due to the extra step being performed, or in order to cover the "microorganisms derived from a living body (I)" with gas bubbles more rapidly and reliably.

Furthermore, it is more preferable to generate "nano-sized or smaller gas bubbles (III)" in the "solvent (II)" in advance.

This is because it is thought that preparing a solution containing (I) using (II) in which (III) is generated in advance makes it possible to minimize the inactivation of the "microorganisms derived from a living body (I)", though a method in which the "solvent (II)" containing the "microorganisms derived from a living body (I)" is prepared and then "nano-sized gas bubbles (III)" are generated therein may also be used.

It should be noted that there is no particular limitation on the used amount of the solvent (II), but a method in which, with respect to about A g of a "biological sample", 1.5 A to 4 A ml (25 to 67 w/v %) of the solvent (e.g., 2 A ml (50 w/v %) of the solvent) is used, or the like is possible, for example.

It should be noted that the amount of (II) can be determined as appropriate based on the condition (e.g., water content) of a "biological sample", and the like.

It is preferable to perform filtration one or more times, and preferably repeatedly perform filtration three or more times.

Donor Type

In particular, when "feces" is used as a "biological sample", there is a tendency to prefer, as a "donor" who provides the "biological sample" from which (I) is to be prepared, a close relative within the second degree of consanguinity of the "recipient" in view of psychological aspects and the like.

However, when top priority is given to treatment efficacy it is thought that it is worthy of consideration not to select a close relative who is considered to also have a similar "balance of resident microorganisms" in light of genetics and the living environment, but rather to purposely select a third-party "donor" who has a completely different "balance of resident microorganisms" from close relatives.

Number of Donors

In order to improve the "balance of resident microorganisms" on a long-term basis, it may be preferable that the number of third-party "donors" is not limited to one, and multiple donors are selected.

Solvent of (II) Used in the Present Invention

There is no particular limitation on the solvent of (II) used in the present invention, and purified water, a physiological saline solution, mineral water, soft drink, or the like may be used.

A physiological saline solution or the like may be used as (II) from the viewpoint of improving compatibility of the "composition containing microorganisms derived from a living body" of the present invention to a living body and engraftment thereof in a living body and in view of an antiseptic effect and the like.

On the other hand, when an apparatus for generating gas bubbles of (III) in the solvent of (II) is made of stainless steel or the like, it may be preferable to use purified water or mineral water from the viewpoint of preventing the apparatus from getting rusty.

Therefore, when the "composition containing microorganisms derived from a living body" of the present invention is manufactured, the same solvent (II) can be consistently used, or different types of solvents (II) can be used in different stages of the manufacturing process.

It should be noted that the "composition containing microorganisms derived from a living body" of the present invention encompasses compositions in the different stages, such as a "stock solution (undiluted solution)" immediately after manufacturing and a "diluted solution" immediately before administration to a "recipient".

Various additives can also be added to the "composition containing microorganisms derived from a living body" of the present invention as long as the effects of the present invention are not inhibited (e.g., as long as the microorganisms derived from a living body of (I) do not die out).

Nano-Sized or Smaller Gas Bubbles of (III) Used in the Present Invention

Preferable examples of a "gas component" in the nano-sized or smaller gas bubbles of (III) used in the present invention include gasses as listed below, but are not necessarily limited thereto.

Kinds of Gasses in Gas Bubbles

It is preferable that the "gas component" in the gas bubbles is constituted by one or more kinds of gasses listed below.

(i) air
(ii) hydrogen
(iii) nitrogen
(iv) ozone
(v) oxygen (vi) carbon dioxide (vii) argon Using air (i) alone is practical and preferable because there is no need to prepare special "gas components" such as those of (ii) to (vii), for example.

It should be noted that, when "air" or "a mixed gas of two or more kinds of gasses" is introduced into the solvent of (II), it is not easy to accurately measure the "ratio between the gas components enclosed" in the "gas bubbles (III) generated in the solvent (II)".

The reason for this is that the "amount" of the gas component that can dissolve in the solvent (II) and the "speed" at which the gas component can dissolve in the solvent (II) depend on the "gas components" in the process in which the gas bubbles (III) are generated in the solvent (II), and it is not easy to accurately determine the "kinds" of and "ratio" between the "gas components" enclosed in the generated gas bubbles (III).

However, when a "gas component" (referred to as "X" for the sake of convenience) constituted by a single kind of gas is used, for example, it is thought that the "ratio of the gas component (X) enclosed" in the "gas bubbles (III) generated in the solvent (II)" should increase compared with a case where a mixed gas such as air is used, and thus the characteristics of the "gas component (X)" as described above can be further utilized.

It should be noted that, when manufacturing the "composition containing microorganisms derived from a living body" in which intestinal bacteria is used, it is preferable to set the ratio of hydrogen in the gas bubbles higher than that of air because the following advantages are expected.

1. The oxidation-reduction potential (target: $-150$ mV$\pm 15$ mV) of nanobubble water of the present invention in which hydrogen is used is as low as the oxidation-reduction potential ($-50$ mV to $-250$ mV) of the intestinal tract, and thus it is thought that bacteria covered with the nanobubble water are likely to engraft in the intestines.

2. When the intestinal tract is inflamed, the oxidation-reduction potential tends to increase, and thus transplanted bacteria are apt to be repelled by the immunity of a recipient due to an increased immune response. However, it is thought that this response can be suppressed by an anti-inflammatory action due to the low oxidation-reduction potential of hydrogen.

3. Both facultative anaerobes and obligatory anaerobes, which are main groups of intestinal bacteria, can be maintained in a state in which they are made inactive but are not killed by using the "nanobubble water" of the present invention that contains hydrogen molecules, and thus it is thought that a bacterial solution can be stored in a state in which the bacteria lie dormant for a relatively long period of time while the balance of the bacteria in the bacterial solution is not disturbed, until the bacteria become active again inside the intestinal tract, which is an appropriate environment, after transplantation.

In order to set the ratio of hydrogen in the gas bubbles higher than that of air, a method of using hydrogen alone as well as a method of using air and hydrogen together, and the like can be used.

In this case, air and a gas including only hydrogen may be enclosed simultaneously but a method in which the concentration of hydrogen enclosed together with air is gradually increased, a method in which only air is used at first and then hydrogen is enclosed in a latter stage, or the like may also be used. It is thought that using these methods makes it possible to minimize the loss of hydrogen due to dissolution in the solvent and enclose a larger amount of hydrogen in gas bubbles.

Although there is no particular limitation on the ratio between air and hydrogen when they are used simultaneously it is thought that it is preferable to set the amount of "(ii) hydrogen" used in an enclosing operation to be ten or more times the amount of "(i) air" used therein, and it is more preferable to set the amount of "(ii) hydrogen" to be one hundred or more times the amount of "(i) air" used therein.

Size of Gas Bubbles

Although the gas bubbles used in the "composition containing microorganisms derived from a living body" of the present invention need to be mainly nano-sized or smaller gas bubbles, the specific size can be changed in accordance with the "microorganisms derived from a living body (I)" that are to be used as circumstances demand.

When the "microorganisms derived from a living body (I)" are viruses, it is preferable that the size of the gas bubbles is smaller than the size of the viruses (commonly 10 to 100 nm) in order to cover the viruses and particularly increase the ratio of engraftment via the mucous membrane and the like.

When the "microorganisms derived from a living body (I)" are bacteria, it is preferable that the size of the gas bubbles is smaller than the size of the bacteria (commonly about 1 μm (1000 nm)) in order to cover the bacteria and particularly increase the ratio of engraftment via the mucous membrane and the like.

When the "microorganisms derived from a living body (I)" are fungi, it is preferable that the size of the gas bubbles is smaller than the size of the fungi (commonly several μm) in order to cover the fungi and particularly increase the ratio of engraftment via the mucous membrane and the like.

Ratio of Nano-Sized or Smaller Gas Bubbles to all Gas Bubbles

"Nano-sized or smaller gas bubbles (III)" need not necessarily account for 100% of the gas bubbles in the "composition containing microorganisms derived from a living body".

However, it is thought that the reason why the "microorganisms derived from a living body (I)" contained in the "composition" of the present invention more reliably engraft in a living body compared with the case of a conventional "composition for transplantation of microorganisms derived from a living body in which a solvent containing no gas bubbles is used" is that "nano-sized or smaller gas bubbles (III)" that are smaller in size than the "microorganisms derived from a living body (I)" cover the "microorganisms derived from a living body (I)" and help them engraft in a living body. Therefore, it is preferable that a large number of "nano-sized or smaller gas bubbles (III)" is contained such that the individual "microorganisms derived from a living body (I)" can be covered.

Furthermore, it is desirable that the ratio of the "nano-sized or smaller gas bubbles (III)" is as high as possible because the denaturation of the composition caused by the collapse of supranano-sized gas bubbles is suppressed, and the engraftment ratio of the "microorganisms derived from a living body (I)" is further increased.

In general, the size of the gas bubbles is not always uniform, and a certain distribution of gas bubble diameters is commonly observed.

Accordingly it is thought that the following can be used as a specific guide: if the "average diameter" of the gas bubbles is smaller than that of the "microorganisms derived from a living body (I)" to be used, there will also be a large number of gas bubbles that are small enough to cover the "microorganisms derived from a living body (I)". For example, when the "microorganisms derived from a living body (I)" are bacteria, the average diameter of the gas bubbles in the solution is preferably smaller than 1000 nm, and more preferably 900 nm or less.

Number of Gas Bubbles in Composition

The larger number of gas bubbles the "composition containing microorganisms derived from a living body" of the present invention contains, the more desirable it is.

Although not necessarily applicable to every case since the specific number of gas bubbles depends on the concentration of (I) (the number of the microorganisms derived from a living body (I)), it was confirmed that several thousand to several hundred million gas bubbles per milliliter, which can be commonly generated by using a known generation apparatus capable of generating the "nano-sized or smaller gas bubbles (III)", is sufficient.

Covering Microorganisms Derived from Living Body (I) with Gas Bubbles

It is thought that the "nano-sized or smaller gas bubbles (III)" naturally adhere to the "microorganisms derived from a living body (I)" so as to cover them by slightly stirring or mixing the solvent (II) containing the gas bubbles and the "microorganisms derived from a living body (I)" together. Also, it is thought that the more sufficiently the "nano-sized or smaller gas bubbles (III)" cover the surround of the "microorganisms derived from a living body (I)", the more rapidly and the more reliably the microorganisms can engraft in a living body without being inhibited by the mucous membrane and the like of the intestinal wall, which includes mucopolysaccharides, etc.

Method for Generating Gas Bubbles

The "nano-sized or smaller gas bubbles of (III)" to be used in the "composition containing microorganisms derived from a living body" of the present invention can be generated through step (1) of a manufacturing method of the present invention, which will be described later.

Method for Manufacturing Composition

The "composition containing microorganisms derived from a living body" of the present invention can be manufactured using the manufacturing method of the present invention, which will be described later.

Dose of "Composition Containing Microorganisms Derived from Living Body" of the Present Invention Although the dose of the "composition containing microorganisms derived from a living body" of the present invention is determined as appropriate depending on the concentration (content ratio) or amount of the "microorganisms derived from a living body (I)" in the composition of the present invention, the "attribute and/or environment" of a "recipient", which will be described later, and the like, it is preferable that approximately 50 ml to 300 ml is administered in each administration.

Number of Administrations of "Composition Containing Microorganisms Derived from Living Body" of the Present Invention The number of administrations of the "composition containing microorganisms derived from a living body" of the present invention is also determined as appropriate depending on the concentration (content ratio) or amount of the "microorganisms derived from a living body (I)" in the composition of the present invention, the "attribute and/or environment" of a "recipient", which will be described later, and the like. Effects may be seen with only a single administration, but, in general, it may be preferable to divide the composition over at least two or more administrations and administer the composition multiple times in order for the microorganisms derived from a living body to reliably engraft in the "recipient". Although there is no particular limitation on the number of administrations in the multiple-dose administration, it may be preferable to perform administration approximately ten times or less in consideration of the burden on the patient, and the like.

It should be noted that, in multiple-dose administration, the length of the administration period, the number of administrations, the amount or concentration (content ratio) of the "microorganisms derived from a living body (I)" in the composition, and the like can be determined as appropriate in consideration of the "attribute and/or environment" of a "recipient", which will be described later, but the original plan can also be flexibly changed as appropriate in light of developments after the administrations.

Moreover, in multiple-dose administration, it may be preferable to perform administration with a concentration gradient by varying the concentration of the "microorganisms derived from a living body (I)" because commonly the microorganisms are likely to be compatible with a living body and can engraft in the living body more reliably.

Administration Period of "Composition Containing Microorganisms Derived from Living Body" of the Present Invention Although the administration period of the "composition containing microorganisms derived from a living body" of the present invention is also determined as appropriate depending on the concentration (content ratio) or amount of the "microorganisms derived from a living body (I)" in the composition of the present invention, the "attribute and/or environment" of a "recipient", which will be described later, and the like, it is preferable to place an interval of several hours to several days between one administration and the subsequent administration in order to improve the engraftment effect. It is preferable to set the entire administration period to one to several months or shorter even when the composition is divided over ten administrations, for example.

The reason for this is that preventing an excessively long interval between the administrations makes it more likely for the effect of continuous administration to be exhibited.

It should be noted that the intervals between the administrations need not be necessarily constant, and various methods are conceivable, such as a method in which the intervals are gradually lengthened or shortened after every administration, a method in which random intervals are set as appropriate in light of the physical constitution and physical condition of a "recipient", the degree of recovery from a disease, and the like.

Kind of "Composition Containing Microorganisms Derived from Living Body" of the Present Invention to be Administered Although the "composition containing microorganisms derived from a living body" can be manufactured as a mixture of microorganisms derived from multiple "donors" from the start of manufacturing, it may be preferable that multiple compositions derived from a single "donor" are manufactured, and then a composition derived from an appropriate "donor" is used as appropriate in each transplantation in light of the physical constitution and physical condition of a "recipient", the degree of recovery from a disease, and the like.

The reason for this is that, as a matter of course, the kind of microorganisms derived from a living body to be introduced varies depending on the physical constitution and physical condition of a "recipient", the degree of recovery from a disease, and the presence or absence of an unexpected accident such as a poor physical condition.

Route of Administration of "Composition Containing Microorganisms Derived from Living Body" of the Present Invention The "composition containing microorganisms derived from a living body" of the present invention can be manufactured as a composition or the like to be administered via the oral cavity, the eyes, the ears, the nose, the vagina, the urethra, the skin, the anus, or the like, and be delivered to an administration target portion using various administration methods.

It should be noted that a composition for engraftment via the "mucous membrane" among the "compositions containing microorganisms derived from a living body" of the present invention is preferable because the advantages of the present invention that can improve the engraftment effect for the microorganisms derived from a living body can be further utilized.

The "mucous membrane" is soft tissue that is mainly present on the inner surface of a hollow organ inside the body, such as a digestive organ, a respiratory organ, a urinary organ, or a reproductive organ, and a specific example is the intestinal mucous membrane that is present on the inside of the intestinal tract and includes mucopolysaccharides and the like.

Instrument for Administering "Composition Containing Microorganisms Derived from Living Body" of the Present Invention Examples of an instrument for administering the "composition containing microorganisms derived from a living body" of the present invention include an "instrument for administering a composition" of the present invention, which will be described later, and known instruments for administering a composition into a living body, such as endoscopic apparatuses (e.g., a large intestine endoscope (colonoscope) and a duodenum endoscope (duodenoscope)) and commercially available intestinal catheters.

Endoscopic apparatuses and the like are preferable because the administration position can be selected in a pinpoint manner. However, it is more preferable that administration is performed using an "instrument for administering a composition" of the present invention or a commercially available intestinal catheter because a preliminary dietary restriction, intestinal tract irrigation, subsequent administration of a purgative, and the like are not needed, and, in particular, a smaller burden is placed on an administration target when a long tube is introduced into the body.

In the administration using an intestinal catheter, a tube that can extend over the entire intestinal tract need not be necessarily used, and the "microorganisms derived from a living body (I)" can sufficiently engraft in a living body even in a case where a tube "with a length of approximately ten and several centimeters (e.g., commercially available rubber intestinal catheter)" is used.

It is thought that the reason for this is that each kind of microorganisms derived from a living body has an inherent biological action potential and has a characteristic in which the same kind of microorganisms derived from a living body that are in the same charged state attract each other, and therefore, microorganisms derived from a living body that are administered via the anus move, by themselves, toward distant resident microorganisms of the same kind in the living body.

Given that the "nano-sized or smaller gas bubbles (III)" are thought to cover the "microorganisms derived from a living body (I)" in the "composition containing microorganisms derived from a living body" of the present invention, it is thus thought that the microorganisms derived from a living body may be more likely to come close to each other due to the biological action potential being amplified by the gas bubbles.

Form of "Composition Containing Microorganisms Derived from Living Body" of the Present Invention, Etc.

The "composition containing microorganisms derived from a living body" of the present invention can be formed in a known composition form as long as collapse of the "nano-sized or smaller gas bubbles (III)" in the composition, inactivation of the "microorganisms derived from a living body (I)", and the like do not occur. A liquid form, the gel form, and the like are preferable, for example.

Examples of typical products of an "oral cavity composition" to be administered via the oral cavity include compositions for treatment such as "medicinal drugs" and "quasi-drugs", "food and beverages", "nutritional supplements", and the like for humans or non-human animals.

Examples of an "ophthalmic composition" include "eyedrops" and the like.

Examples of an "otorhinological composition" include "nasal drops (collunarium)" and the like.

Examples of a "composition for dermal administration" include "patches" such as "cataplasms", and "topical products" such as "ointments" and "sprays".

Examples of a composition to be administered via the anus include compositions for treatment such as "medicinal drugs" and "quasi-drugs".

Composition for Adjusting Balance of Resident Microorganisms of the Present Invention A "composition for adjusting the balance of resident microorganisms" of the present invention includes the above-described "composition containing microorganisms derived from a living body" of the present invention.

The reason for this is that the "composition containing microorganisms derived from a living body" of the present invention is useful to adjust the balance of microorganisms in a living body (e.g., the kinds and ratio between the kinds of microorganisms) that has been disrupted due to a disease and the like.

In particular, it is preferable to use the "composition containing microorganisms derived from a living body" as a main component of a "composition for adjusting the intestinal flora balance".

It should be noted that the "balance of resident microorganisms" may refer to the "balance of all the resident microorganisms" in the living body of an individual, or may refer to the "balance of resident microorganisms in a specific organ in the living body", and the "composition for adjusting the balance of resident microorganisms" of the present invention is particularly useful to adjust the "balance of resident microorganisms" in a specific organ, particularly the "balance of resident microorganisms living in the intestines", namely the "intestinal flora balance".

The specific constitution thereof may be the same as that of the above-described "composition containing microorganisms derived from a living body", or may further contain another component that is useful to adjust the balance of resident microorganisms.

The "dose", "number of administrations", "administration period", "administration route", "administration instrument", "form", and the like of the "composition for adjusting the balance of resident microorganisms" of the present invention are as described in the description of the "composition containing microorganisms derived from a living body" of the present invention.

Method for Manufacturing Composition of the Present Invention

Methods for manufacturing the "composition containing microorganisms derived from a living body" and "composition for adjusting the balance of resident microorganisms" of the present invention (these may be collectively referred to as "composition of the present invention" hereinafter) include at least steps (1) and (2) below.

(1) A step of generating gas bubbles of (III) in a solvent of (II).
(2) A step of dispersing and/or dissolving (I) in (II).
(I) At least one or more kinds of microorganisms derived from a living body
(II) Solvent
(III) Nano-sized or smaller gas bubbles (also referred to as "nanobubbles" hereinafter)

Order of Steps

Although the above-mentioned steps may be performed in the order of (2) and (1), it is preferable to perform them in the order of (1) and (2) from the viewpoint that the risk of inactivation of the microorganisms derived from a living body during the manufacturing process can be minimized.

Moreover, other steps can be additionally performed before and after these steps.

Technique for Step (1)

Examples of a method for "generating gas bubbles of (III) in a solvent of (II)" in step (1) include, but are not limited to, the following techniques and methods in which these techniques are used in combination.

Gas-Liquid Mixture Shearing Technique:

This is a technique in which gas is rotated at a high speed together with a liquid.

Ultrasonic Technique:

This is a technique in which a shock wave is applied to or cavitation is allowed to occur in a liquid to further collapse gas bubbles that have been generated.

Pressurized Dissolution Technique:

This is a technique in which gas bubbles are generated by pressurizing gas and a liquid and discharging them in one burst.

Micropore Technique:

This is a technique in which gas is supplied while pressure is applied thereto using an orifice or the like.

Electrolytic Technique:

This is a technique in which gas is generated from a thin wire immersed in an aqueous solution.

Among the above-mentioned techniques, the "gas-liquid mixture shearing technique" is preferable because stable nano-sized or smaller gas bubbles can be generated by further performing shearing processing on microbubbles.

Specifically nanobubbles can be generated by using commercially available apparatuses of 1) and 2) below together, for example.

1) Generation of gas bubbles with a diameter of 1 micrometer or less using a micro-nanobubble generation apparatus "BUVITAS (registered trademark) HYK-25" manufactured by Kyowa Kisetsu (rotation shearing technique).
2) Formation of nanobubbles from micro-nanobubbles using "vG7 (registered trademark)" manufactured by AYAWA Co., Ltd. (stainless-steel filter).

Technique for Step (2)

Examples of a method for "dispersing and/or dissolving (I) in (II)" in step (2) include a method in which the "microorganisms derived from a living body (I)" are processed using the "solvent(II) containing the gas bubbles (III)" prepared in step (1) above, and the like.

As also described in the above-described section "Method For Processing Biological Sample", the term "process" means that a "biological sample" containing target "microorganisms derived from a living body (I)" that has been extracted from the living body of a "donor" is slightly stirred in the "solvent (II) containing the gas bubbles (III)" and then unnecessary substances other than (I) are removed through a technique such as filtration, or that "microorganisms derived from a living body (I)" that have been purified in advance are diluted by a solvent such as the "solvent (II) containing the gas bubbles (III)", for example.

It should be noted that the amount of the solvent (II) to be used, the number of filtrations, and the like are as described in the above-described section "Method For Processing Biological Sample".

It should be noted that a process is also possible in which the above-mentioned processing is performed using the "solvent (II)" instead of the "solvent (II) containing the gas bubbles (III)" and then the gas bubbles (III) are generated in the solvent (II). However, it is preferable to perform the processing using the "solvent (II) containing the gas bubbles (III)" in order to minimize the inactivation of the "microorganisms derived from a living body (I)".

Addition of Step (3)

The method for manufacturing the "composition of the present invention" can include a step of (3) below together with (1) and (2).

(3) A step of determining the kinds of and the ratio between the kinds of microorganisms derived from a living body in (I), and/or one or more individuals from which (I) is collected, depending on the "attribute and/or environment" of a "recipient".

The "attribute" encompasses the properties, characteristics, and the like of a "recipient", such as the physical condition of the recipient, the type of disease from which the recipient is suffering and the severity thereof, the age, the sex, the height, the weight, the somatotype, the blood pressure, the medical history and the lifestyle thereof, including eating/drinking habit and smoking habit.

The "environment" encompasses the living environment and the like, including the climate zone, temperature, humidity and the presence or absence of cigarette smoke, exhaust gas, and the like in the living area in which the "recipient" lives or works, as well as the family structure, the occupation, whether or not the recipient has a pet, and the season and climate when administration is performed.

When the "microorganisms derived from a living body (I)" are collected from a healthy "donor" as a "mass" to a certain extent and used as they are (e.g., the entirety of an aggregate of multiple kinds of resident microorganisms in a biological sample, such as the entire "intestinal flora"), a step such as (3) above is not necessarily needed in particular. However, when a mixture of "masses" collected from multiple "donors" is used, or the ratio of a specific resident microorganism purposely needs to be significantly changed depending on the type of disease or other conditions, for example, it may be preferable to add a step such as (3).

It should be noted that when the step of (3) is performed, this step may be performed before or after the step of (2).

Method for Determining Constitution of Composition of the Present Invention

A method for determining the constitution of the "composition of the present invention" includes the following steps.

(A) A step of estimating a kind of "balance of microorganisms derived from a living body" to be administered.

(B) A step of selecting "microorganisms derived from a living body" collected from one or more individuals that may or may not include an administration target, such that the "kind of the balance of microorganisms derived from a living body" estimated in (A) can be achieved.

It should be noted that the "constitution" as used in the present invention collectively refers to "the kinds of and the ratio between the kinds of microorganisms in the microorganisms derived from a living body (I)" and "the concentration (content ratio) of the microorganisms derived from a living body (I)" in the composition of the present invention as well as the kind and content ratio of the "solvent (II)", the "diameter" of the "nano-sized gas bubbles (III)", the "kinds of gas components" in the "nano-sized gas bubbles (III)", and the "number of the nano-sized gas bubbles (III)", and the like.

"The kinds of and the ratio between the kinds of microorganisms in the microorganisms derived from a living body (I)" and the "diameter" of the "nano-sized gas bubbles (III)" and the "number of the nano-sized gas bubbles (III)"

are particularly important for the composition of the present invention.

"Estimating the kind of balance of microorganisms derived from a living body" in the step of (A) means that, when an aggregate of multiple kinds of microorganisms derived from a living body is used as the "microorganisms derived from a living body (I)", the ratio of one or more specific kinds of microorganisms therein are used as indexes to envision, for each administration target (patient), an ideal "balance of microorganisms derived from a living body" that is considered to be useful to treat a disease from which the administration target suffers.

The following are specific examples of items to be investigated for envisioning.

(A)-i:

The "balance of resident microorganisms" in an administration target.

The "balance of resident microorganisms" refers to the kinds of resident microorganisms, the ratio (number ratio) between the kinds of resident microorganisms, and the like in "the entirety of an individual" or "a specific organ in a living body".

Various known methods can be used as a method for measuring the "balance of resident microorganisms", but there is no particular limitation thereto. For example, a method in which "characteristic genes" of resident microorganisms are measured using a DNA sequencer or the like can be used.

However, since it has been revealed that there is a certain correlation between a "physical condition, disease" or the like and the characteristics of the "intestinal flora balance", for example, (A)-i need not be necessarily investigated if a physical condition or the type and severity of a disease are investigated as the attribute of a "recipient" in (A)-iii, which will be described later, for example.

(A)-ii:

The tendency of the "balance of resident microorganisms" in another individual that is not considered to suffer from at least that disease.

When it is determined from the results of the analysis in (A)-i or the like that the amount of a specific "intestinal bacterium A" is significantly small in the "balance of resident microorganisms" in the administration target compared with the tendency of the ratio of A in the balance of resident microorganisms in a healthy individual, a "balance of microorganisms derived from a living body" that contains a sufficient amount of the "intestinal bacterium A" is envisioned as an ideal "balance of microorganisms derived from a living body" to be administered.

In addition to this, the kind of "balance of microorganisms derived from a living body" to be administered, which is estimated in the step of (A), can be modified by further confirming or investigating the following items, for example.

(A)-iii:

The "attribute and/or environment" of an administration target ("recipient").

It should be noted that the "attribute and/or environment" as used herein refers to those described in the above-described section "Method For Manufacturing Composition Of The Present Invention".

(A)-iv:

Findings obtained from the results of treatment using "transplantation of microorganisms derived from a living body" that have been accumulated so far.

In the step of (B), "microorganisms derived from a living body" collected from one or more individuals that may or may not include a "recipient" are selected, such that the kind estimated in (A) can be achieved.

Specifically, the step of (B) can be implemented by determining resident microorganisms in a recipient that are larger (or smaller) in amount compared with the "balance of resident microorganisms" in one or more healthy individuals and selecting "microorganisms derived from a living body" collected from one or more individuals in which the balance of these microorganisms is favorable.

Instrument for Administering Composition of the Present Invention

An "instrument for administering the composition" of the present invention is an example of an instrument for administering, via the anus or the like, the above-described "composition of the present invention" such as the "composition containing microorganisms derived from a living body" or the "composition for adjusting the balance of resident microorganisms", and includes a "tubular portion".

For example, tubular articles and the like such as commercially available intestinal catheters can be used as the "tubular portion".

It should be noted that the length of the "tubular portion" varies depending on the age, the somatotype, and the like of a "recipient", but is preferably 5 cm or more, more preferably 10 cm or more, even more preferably 15 cm or more, and particularly preferably 18 cm or more, for example.

However, a long tubular portion that can extend over the entire intestinal tract need not be necessarily used, and it may be preferable that the length is 50 cm or less, for example, in order to avoid a risk of a change in physical properties of the "composition" or the like due to the tubular portion being conversely too long.

The above-mentioned instrument can include the following portions.

"Storage Portion": A portion such as a "main body" of a syringe, a "tank" attached to a large intestine endoscope, and a "liquid medicine container" of an irrigator or instillation pack in which the "composition" of the present invention can be stored.

"Extrusion Mechanism": A mechanism such as a pump that can extrude the "composition" in the "storage portion".

It should be noted that, as a disposable enema container such as a mini enema (Ichijiku enema), the "storage portion" may be formed to function as a mechanism that can extrude the object stored in the storage portion.

Assistant Solvent for Introduction into Living Body of the Present Invention

An "assistant solvent for introduction into a living body" of the present invention contains (II) and (III) below, and is also referred to as "nanobubble water" in the present invention.

(II) Solvent
(III) Nano-sized or smaller gas bubbles

It should be noted that "introduction into a living body" means that the introduced substance is brought into a state of being capable of exhibiting its function in a living body through engraftment or attachment as well as by being allowed to be present inside or outside the blood vessels, in cavities in the living body (in the intestinal tract), and the like, for example.

Specific examples of the administration route include routes via the oral cavity, the eyes, the ears, the nose, the vagina, the urethra, the skin, and the anus. Of these, the introduction via the mucous membrane is preferable, and the introduction via the intestinal wall is particularly preferable.

Examples of a substance targeted for facilitation of introduction into a living body by the "assistant solvent for introduction into a living body" mainly include organic substances. Of these, microorganisms derived from a living body are preferable, and intestinal bacteria are particularly preferable. Inorganic substances such as minerals may also be used.

It should be noted that, when "microorganisms derived from a living body" are used as the substance targeted for facilitation of introduction into a living body, introducing the "microorganisms derived from a living body" into the "mucus" on the mucous membrane by using the "assistant solvent for introduction into a living body" of the present invention allows organic acids and the like produced by the microorganisms derived from a living body to penetrate deeply in a living body via the "mucous membrane".

As is clear from Test Examples, which will be described later, and the like, using the "assistant solvent for introduction into a living body" of the present invention makes it possible to more efficiently introduce, into a living body, a substance to be introduced.

Agent for Improving Physical Constitution and/or Physical Condition of the Present Invention An "agent for improving a physical constitution and/or physical condition" of the present invention specifically contains the following.

(I) At least one or more kinds of microorganisms
(II) Solvent
(III) Nano-sized or smaller gas bubbles As is clear from Test Examples, which will be described later, and the like, introducing the "agent for improving a physical constitution and/or physical condition" of the present invention makes it possible to improve the physical constitutions and/or physical conditions of many patients who suffer from diseases and poor physical conditions, and can thus be useful to prevent and/or treat diseases.

Method for Improving Physical Constitution and/or Physical Condition of the Present Invention A "method for improving a physical constitution and/or physical condition" of the present invention is a method in which the composition according to the present invention is introduced into a living body to prevent and/or treat a disease, or improve a physical constitution and/or physical condition.

As is clear from Test Examples, which will be described later, and the like, the "method for improving a physical constitution and/or physical condition" of the present invention can improve the physical constitutions and/or physical conditions of many patients who suffer from diseases and poor physical conditions, and can thus be useful to prevent and/or treat diseases.

Method for Introducing Objective Substance into Living Body of the Present Invention In a "method for introducing an objective substance into a living body", the above-mentioned "assistant solvent for introduction into a living body" of the present invention is used.

As is clear from Test Examples, which will be described later, and the like, the "method for introducing an objective substance into a living body" makes it possible to more efficiently introduce an objective substance into living bodies of many patients who suffer from diseases and poor physical conditions compared with a conventional method.

EXAMPLES

Before examples of the "composition containing microorganisms derived from a living body" of the present invention are described, details of the "assistant solvents for introduction into a living body" of the present invention, namely the "(II) solvent" containing the "(III) nano-sized or smaller gas bubbles" (referred to as "nanobubble water" hereinafter), which were used in the examples, and the "intestinal flora balance" will be described.

Example A: Assistant Solvent For Introduction Into Living Body

Materials And Methods

Manufacturing of "Nanobubble Water A"

An "assistant solvent A for introduction into a living body (nanobubble water A)" of the present invention was produced using mineral water and air with the above-described apparatus and the like.

The "nanobubble water A" produced as mentioned above was diluted 250 fold for the convenience of measurement of the diameters of the gas bubbles, and the size of the gas bubbles, the number of the gas bubbles, and the like in the diluted solution were measured using "Multisizer 3" manufactured by Beckman Coulter.

FIG. 1 shows the results.

The uppermost line graph indicated by "*" in the diagram shows the results from the analysis of the "nanobubble water A" used in the present invention.

Analysis Results Shown in FIG. 1:

Average diameter of gas bubbles: 830 nm
Number of gas bubbles: about 435 thousand per milliliter Accordingly it is considered that the number of the gas bubbles in 1 ml of the "nanobubble water A" (not diluted 250 fold) used in the present invention was approximately a hundred million.

Example B: Assistant Solvent for Introduction into Living Body

An "assistant solvent B for introduction into a living body (nanobubble water B)" of the present invention was manufactured in the same manner as in Example A, except that hydrogen and air were used together as gas to be enclosed when gas bubbles were generated, and hydrogen was enclosed in the latter stage of the enclosing process to increase the hydrogen concentration in gas bubbles.

It should be noted that the amount of hydrogen used in the enclosing process was about 250 times as large as the amount of air.

It is considered that the number of the gas bubbles in 1 ml of the "nanobubble water B" (not diluted 250 fold) used in the present invention was also approximately a hundred million.

Measurement of "Intestinal Flora Balance"

"The kinds of and the ratio (number ratio) between the kinds of intestinal bacteria" in a solution obtained by filtering and purifying feces collected from each of "donors" and "recipients" were measured using known genes specific to respective intestinal bacteria as indices, and thus an "intestinal flora balance" of each individual was obtained.

The genes specific to respective intestinal bacteria were measured using the following apparatus.

DNA Sequencer: "MiSeq" manufactured by Illumina K.K.

Example 1: Composition Containing Microorganisms D (Intestinal Bacteria) Derived from Living Body (Undiluted Solution)

Establishment of Intestinal Flora Bank

The "intestinal flora balances" in feces derived from about 80 "donors" (healthy humans) were measured, and the "compositions containing microorganisms derived from a living body (undiluted solution)" of the present invention were manufactured using the feces and the above-described "nanobubble water A" (not diluted 250 fold). Thus, an "intestinal flora bank" was established.

Specifically, "50 to 150 g" of feces collected from each "donor" was immersed in 1.5 to 4 times the amount of, namely "75 to 600 ml" of, the "nanobubble water A" (not diluted 250 fold) and partially dissolved, for example, under slight stirring, and then naturally dissolved completely.

It should be noted that the amount of the "nanobubble water A" was determined as appropriate depending on the condition (e.g., water content) of feces of the "donor" and the like.

Next, this solution was filtered more than once using sterilized gauze until unnecessary substances such as food residue were not confirmed under an optical microscope (low magnification), and a "composition containing microorganisms derived from a living body (Undiluted Solution)" was manufactured for every donor.

It should be noted that the sterilized gauze was provided with pores having a size that allows the "microorganisms derived from a living body (I)" and the "nanobubbles (III)" to pass therethrough.

Examples 2 to 9: Composition Containing Microorganisms (Intestinal Bacteria) Derived from Living Body (Diluted Solution)

(A) Estimation of Kind of "Intestinal Flora Balance" to be Administered (A)-i: Measurement of "Balance of Resident Microorganisms (Intestinal Flora)" of Administration Target Patients suffering from various diseases shown in FIGS. 2 to 9 were selected as administration targets.

Feces was collected from each patient (referred to as "recipient" hereinafter), and the "intestinal flora balance" was measured by analyzing the genes of intestinal bacteria.

FIGS. 2 to 9 show the results (the left bars in the bar graphs).

(A)-ii: Confirmation of Tendency of "Intestinal Flora Balance" of "Donors"

For each "recipient", the tendency of "intestinal flora balance" of "donors" who were not considered to suffer from at least a disease from which the "recipient" suffered was confirmed.

After the "intestinal flora balance" of the "recipient" measured in (A)-i and the tendency confirmed in (A)-ii were compared, the "attribute and/or environment" of the "recipient" described in (A)-iii as well as the findings about "intestinal flora transplantation" that had been accumulated described in (A)-iv were further taken into consideration collectively and thus the kind of "intestinal flora balance" to be administered to the recipient was estimated.

(C) Selection of "Intestinal Flora" Derived from Healthy "Donor"

For each "recipient", four to six "donors" who had "intestinal flora" that could achieve the "kind of the balance of resident microorganisms" determined in (B) were selected from the above-described "intestinal flora bank".

Manufacturing of Composition Containing Microorganisms Derived from Living Body (Diluted Solution)

For each of the "recipients" suffering from various diseases shown in FIGS. 2 to 9, four to six kinds of "compositions containing microorganisms derived from a living body (undiluted solution)" were mixed (mixture of undiluted solutions).

Then, the mixture of undiluted solutions manufactured for each "recipient" was diluted using a physiological saline solution to provide multiple solutions of various concentrations, and thus multiple "compositions containing microorganisms (intestinal bacteria) derived from a living body (diluted solutions)" that provided a concentration gradient of about 5- to 50-fold dilution were obtained.

FIGS. 2 to 9 show the "intestinal flora balance" of the "composition containing microorganisms (intestinal bacteria) derived from a living body (diluted solution)" derived from multiple "donors" selected for each of the various diseases (the right bars in the bar graphs).

Example 10: Instrument for Administering Composition Containing Microorganisms (Intestinal Bacteria) Derived from Living Body An "administration instrument" for the composition of the present invention was manufactured using a 12-fr (French: outer diameter) to 15-fr intestinal catheter (with a length of about 50 cm) as the "tubular portion", and an enema container, irrigator, or instillation pack, in which the intestinal catheter was linked to its leading end, as the "storage portion" for the composition.

The outer diameter of the "tubular portion" and the kind of "storage portion" were determined depending on a composite factor including the age, sex, symptom, and the like of the "recipient".

When the "recipient" was an infant, a 12-fr intestinal catheter was used, and when the "recipient" was an adult, a 12- to 15-fr intestinal catheter was used.

Test Example 1: Test to Confirm Engraftment of Microorganisms Derived from Living Body—a Administration to "Recipient" (Patient)

The "compositions containing microorganisms (intestinal bacteria) derived from a living body (diluted solutions)" manufactured in Examples 2 to 9 were administered to respective "recipients".

Specifically the intestinal catheter portion of the above-mentioned instrument in Example 10 was inserted into the "recipient" via the anus to approximately 17 to 20 cm, and 50 to 300 ml of the "composition containing microorganisms derived from a living body (diluted solution)" of the present invention was transplanted using an intestinal infusion technique.

The insertion length was determined as appropriate depending on the age, somatotype, symptom, and the like of the "recipient", and the transplantation amount was determined as appropriate depending on the age, symptom, number of administrations, or the like.

It should be noted that the transplantation was performed by administering the above-described approximately 5- to 50-fold diluted solution with a concentration gradient being formed by changing the concentration of the microorganisms derived from a living body contained in the solution in 1 to about 10 divided doses over 1 day to several months while the improvement degree of a disease, the physical condition, and the like of the "recipient" was confirmed.

Results: Change in "Intestinal Flora Balance"

Feces was collected from each "recipient" after the transplantation was performed in 1 to 10 divided doses (after the transplantation period had finished), and the "intestinal flora balance" was measured by analyzing the genes of intestinal bacteria.

FIGS. 2 to 9 show the results (the central bars in the bar graphs).

In all the cases shown in FIGS. 2 to 9, it was revealed that the "intestinal flora balance (the central bar in the bar graph)" of the "recipient" was significantly improved, and came considerably close to the "intestinal flora balance" of the "donor" (the right bar in the bar graph).

It may be considered that the change in the "intestinal flora balance" after the transplantation resulted from the fact that the transplanted composition did not engraft and was directly excreted.

However, the absolute amount of bacteria contained in the transplanted composition was far smaller than that of intestinal bacteria in the "recipient" him/herself, and therefore, it is reasonable to think that the reason why the "intestinal flora balance" in feces after the end of the transplantation period changed significantly as shown in the diagrams is that logarithmic amplified growth of bacteria that engrafted under the intestinal mucous membrane was repeated, and the bacteria were excreted to feces as bacteria of the "recipient's" own.

Accordingly it is thought that the "intestinal flora balance" after the transplantation, which is shown in FIGS. 2 to 9 (central bars in the bar graphs), resulted from the fact that the transplanted microorganisms derived from a living body surely engrafted in the living body of the "recipient".

It should be noted that it has been reported that in the case of conventional "intestinal flora transplantation" (in which the "nanobubble water A" is not used), the change in the "intestinal flora balance" after the transplantation is small and the improvement degree of a disease is not satisfactory.

In contrast, according to the above-mentioned test results, the "intestinal flora balance" in feces was obviously improved after the administration and came considerably close to the "intestinal flora balance" of the healthy "donor".

That is, the above-mentioned test results are surprising compared with the conventional "intestinal flora transplantation".

Discussion

The above-mentioned results show that, by using "nano-sized or smaller" gas bubbles, the intestinal bacteria, which are the "microorganisms derived from a living body of (I)", could more reliably engraft and proliferate in the intestines and form an "intestinal flora" with a new balance of resident microorganism, that is, the "compositions containing microorganisms derived from a living body" of Examples 2 to 9 functioned as a "composition for adjusting the balance of resident microorganisms".

It is thought to be likely that minute gas bubbles that may cover microorganisms derived from a living body impaired the function exhibited by the mucous membrane, which include mucopolysaccharides, etc., of the intestinal tract, and the like, of preventing the entry of substances from the outside into the inside of a living body.

Accordingly among the "compositions of the present invention", a composition for engraftment in the living body of a "recipient" via the mucous membrane is of particularly high utility value.

Test Example 2: Test to Confirm Engraftment of Microorganisms Derived from Living Body—b Administration of Human Intestinal Flora to Mouse A "composition containing microorganisms derived from a living body" (undiluted solution) was produced using human feces in the same manner as in Example 1, except that the nanobubble water B was used instead of the nanobubble water A. Next, the "compositions containing microorganisms derived from a living body" (diluted solutions) of the present invention were produced in the same manner as in Examples 2 to 9.

For comparison, "compositions containing microorganisms derived from a living body" (diluted solutions) for comparison were produced in the same manner using a conventional method in which a physiological saline solution was used instead of nanobubble water.

Then, 2 cc of each of the "compositions containing microorganisms derived from a living body" (diluted solutions) of the present invention and the conventional method was introduced into three mice, respectively.

Backflow was minimized by hanging the mice upside down while catching their tails and introducing the compositions from above into the intestines using an intestinal infusion technique.

Collection of Mouse Feces

The mice were placed in cages after the transplantation, and feces were respectively collected before the administration, immediately after the administration, on the next day (around 9:00 a.m. and around 5:00 p.m), after two days (around 9:00 a.m. and around 5:00 p.m), after three days (around 9:00 a.m. and around 5:00 p.m), and after seven days (around 9:00 a.m. and around 5:00 p.m). The feces were chilled and stored, and then the intestinal floras were analyzed using a next-generation sequencer (Miseq manufactured by Illumina K.K.).

Results: Change in "Intestinal Flora Balance"

On the seventh day, the number of bacteria belonging to the "genus Blautia" drastically increased irrespective of the intestinal flora balance of the transplanted "composition containing microorganisms derived from a living body".

It should be noted that the increasing ratio of bacteria belonging to the "genus Blautia" in the case of the "compositions containing microorganisms derived from a living body" of the present invention was significantly high compared with the case of the "compositions containing microorganisms derived from a living body" of the conventional method.

Discussion

It has been reported that, when an organ or the like is transplanted, bacteria belonging to the "genus Blautia" drastically proliferates to protect the host, and contributes to a reduction in a case fatality rate of a graft-versus-host disease (Biology of Blood and Marrow Transplantation Volume 21, Issue 8, August 2015, Pages 1373-1383).

Accordingly the above-described results are thought to attest that at least a portion of the transplanted "human intestinal flora" surely "engrafted" in the intestines of the mice, and furthermore, the "engraftment amount" was significantly larger than in the case of the conventional method.

It should be noted that, no matter what method is used, such a drastic increase in the number of bacteria belonging to the "genus Blautia" is not observed in the case of transplantation between humans. However, utilizing such a change specific to "transplantation between animals of different species" made it possible to confirm an excellent engraftment effect of the "compositions containing microorganisms derived from a living body" of the present invention.

Test Example 3-1: Test to Confirm Effect of Improving Physical Constitution and/or Physical Condition—Case 1

Case 1: Man aged 34 years
Diagnosis: Giardiasis
Chief Complaint: Nausea
Present Illness: He had stayed in India for two months in 2011. He had been suffering from diarrhea since he ate fruits (tap water was used) during the stay. Even after he returned to his mother country (the United States), he suffered from digestive upsets such as diarrhea, nausea, and the like. As a result of a close examination, he was diagnosed as having giardiasis caused by *Giardia lamblla*, and antibiotics were intermittently administered for six months. Thereafter, giardiasis was cured in light of an examination result, but after several months to one year, he began feeling ill when ingesting sugar. In particular, the symptom was prominent when he ingested food such as dessert in which refined sugar was used, alcohol, and milk (yogurt was no problem), but food such as fruits that contains dietary fiber was no problem. He had the symptoms after eating a large amount of white rice, but had no symptoms after eating whole wheat flour.
Medical History: No appreciable disease
Test Method for Confirming Effect of Improving Physical Constitution and/or Physical Condition
The constitutions of the "compositions containing microorganisms derived from a living body" used in transplantation, and the protocol for the implemented intestinal flora transplantation were shown in the following description and FIG. 10A.

Constitution of "Composition Containing Microorganisms Derived from Living Body"

As described below, "compositions containing microorganisms derived from a living body" to be used in transplantation in UB1 to UB3 in the protocol were prepared.

UB1: A diluted solution was prepared by diluting, with 250 ml of a physiological saline solution, 5 ml of an undiluted solution obtained by treating feces derived from a donor B shown in FIG. 10B with the nanobubble water B.

UB2: A diluted solution was prepared by diluting, with 250 ml of a physiological saline solution, 8 ml of an undiluted solution obtained by treating feces derived from a donor B shown in FIG. 10B with the nanobubble water B.

UB3: A diluted solution was prepared by diluting, with 250 ml of a physiological saline solution, 10 ml of an undiluted solution obtained by treating feces derived from a donor A shown in FIG. 10B with the nanobubble water B.

Protocol

1. Examining intestinal flora (feces) before transplantation (1).
2. Transplanting feces selected from the flora bank using an intestinal infusion technique after adjusting a bacterial solution for transplantation using a physiological saline solution (S1).
3. Examining intestinal flora (feces) after two weeks (2).
4. Then, transplanting feces using an intestinal infusion technique after adjusting a bacterial solution using ultra fine bubble water (nanobubble water B) (UB1).
5. Transplanting feces using ultra fine bubble water (nanobubble water B) once every week, three times in total (UB2, UB3).
6. Examining intestinal flora (feces) after two weeks (3).
7. Grasping changes in the symptoms by a medical interview.

Follow-up
S1 to (2)

He had a strong feeling of fullness in the abdomen after the transplantation in S1, and had difficulty in taking a meal. He had diarrhea three days after the transplantation, and it continued for three days.

UB1 to UB2

He had no feeling of fullness in the abdomen after UB1. He did not have diarrhea, and was in good physical condition.

UB2 to UB3

The physical condition was improving. He had a normal bowel movement (formed stool was excreted once every day).

UB3 to (3)

He was in good physical condition. He started eating food that had been causing the symptoms little by little, but he had no symptoms.

Figure 10B:
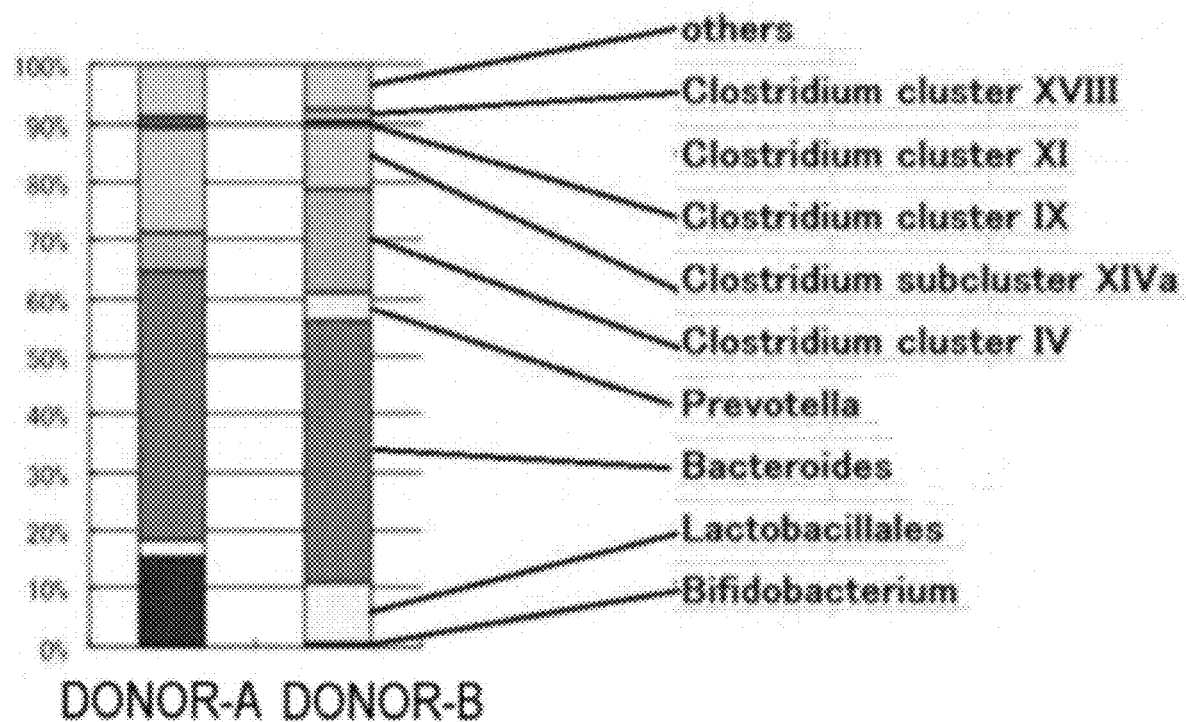
FIG. 10B is a diagram showing a change in the intestinal flora of a "recipient" (patient suffering from giardiasis) when administering a composition of the present invention (intestinal flora derived from "donors"), in which feces were corrected at the times (1)-(3).
Figure 10B:
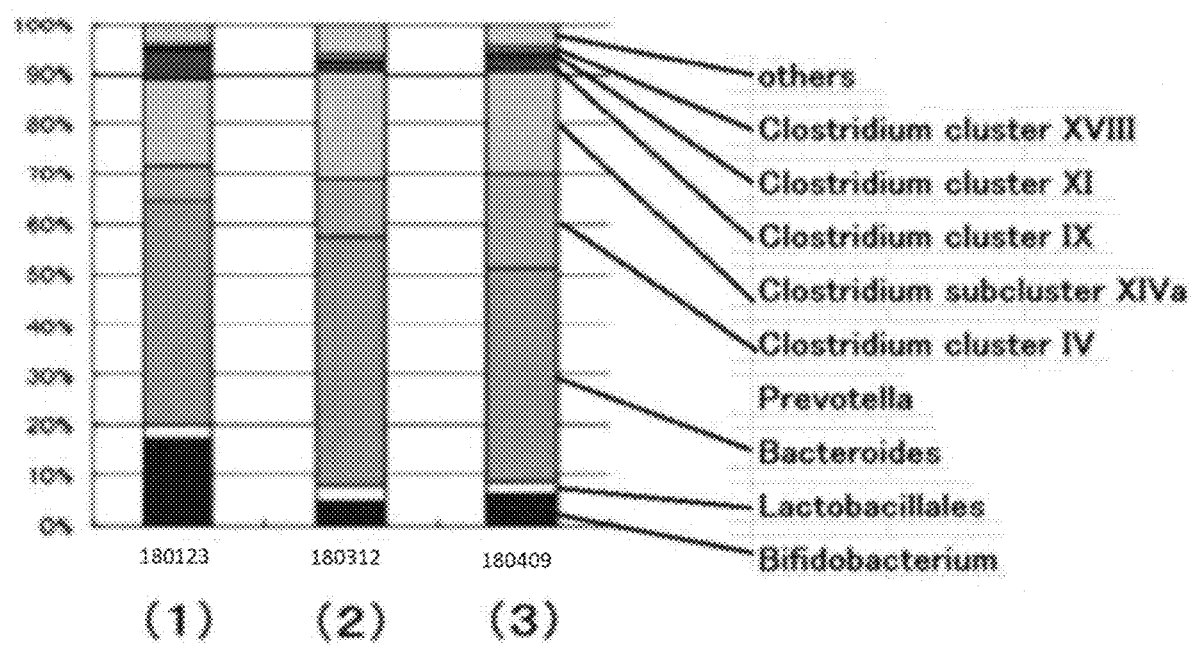

FIG. 10B shows the results from the examination of the intestinal flora balance in feces collected in (1), (2), and (3) above.

Results

As shown in FIG. 10B, after implementing the transplantation (UB1 to UB3) of the compositions containing microorganisms derived from a living body of the present invention in which the nanobubble water B were used, *Clostridium* cluster XI, which was not confirmed after the implementation of S1, appeared, and the ratio of the genus *Clostridium* in the entirety increased.

This suggests that the immunoregulation and mental symptoms were improved. Regarding the overall balance, the overexpression of *Bacteroides* was suppressed, and it is thus thought that an improving trend was indicated due to the transplantations of the compositions containing microorganisms derived from a living body of the present invention (UB1 to UB3).

Discussion

The physical condition rather became worse when the conventional method S1 was implemented first, whereas the physical condition smoothly recovered after the implementation of UB1. Therefore, it is clear that the "compositions containing microorganisms derived from a living body" of the present invention in which the nanobubble water B is used are more useful than the conventional "composition containing microorganisms derived from a living body" obtained by dissolving microorganisms derived from a living body in only a physiological saline solution, and can be used as an "agent for improving a physical constitution and/or physical condition".

Test Example 3-2: Test to Confirm Effect of Improving Physical Constitution and/or Physical Condition—Case 2

Case 2: Man aged 52 years
Chief Complaint: Chronic fatigue symptom
Medical History: Surgical removal of the vermiform appendix (in his twenties); Lumbar disc herniation (in his thirties)
Present Illness: He was conscious of fatigue symptoms in the afternoon, though his daily life was not adversely affected. He participated, as a subject, in a clinical trial for the purpose of evaluating the engraftment ratio in transplantation of feces.

Test Method for Confirming Effect of Improving Physical Constitution and/or Physical Condition The constitutions of the "compositions containing microorganisms derived from a living body" used in transplantation, and the protocol for the implemented intestinal flora transplantation were shown in the following description and FIG. 11A.

Constitution of "Composition Containing Microorganisms Derived from Living Body"

As described below, "compositions containing microorganisms derived from a living body" to be used in each transplantation in UB1 to UB3 in the protocol were prepared.

UB1: A diluted solution was prepared by diluting, with 250 ml of a physiological saline solution, 5 ml of an undiluted solution obtained by treating feces derived from a donor D shown in FIG. 11B with the nanobubble water B.

UB2: A diluted solution was prepared by diluting, with 250 ml of a physiological saline solution, 8 ml of an undiluted solution obtained by treating feces derived from a donor C shown in FIG. 11B with the nanobubble water B.

UB3: A diluted solution was prepared by diluting, with 250 ml of a physiological saline solution, 10 ml of an undiluted solution obtained by treating feces derived from a donor D shown in FIG. 11B with the nanobubble water B.

Protocol

1. Examining intestinal flora (feces) before transplantation (1).
2. Transplanting feces selected from the flora bank using an endoscope after adjusting a bacterial solution for transplantation using a physiological saline solution (S1).
3. Examining intestinal flora (feces) after two weeks (2).
4. Then, transplanting feces using an intestinal infusion technique after adjusting a bacterial solution using ultra fine bubble water (nanobubble water B) (UB1).
5. Transplanting feces using ultra fine bubble water (nanobubble water B) once every week, three times in total (UB2, UB3), and examining intestinal flora (feces) after each transplantation ((3), (4), (5)).
6. Grasping changes in the symptoms by a medical interview.

Follow-Up

S1 to UB1

Since the day following the implementation of S1, in addition to a feeling of fatigue, borborygmus caused by hyperperistalsis in the abdomen, and abdominal discomfort intermittently continued.

UB1 to UB3

The abdominal discomfort disappeared immediately after the implementation of UB-1, and the symptoms of which he was conscious, such as a feeling of malaise, improved.

After UB-3

Although he was conscious of a slightly large amount of gas, he had no abdominal discomfort and no feeling of malaise.

Figure 11B:
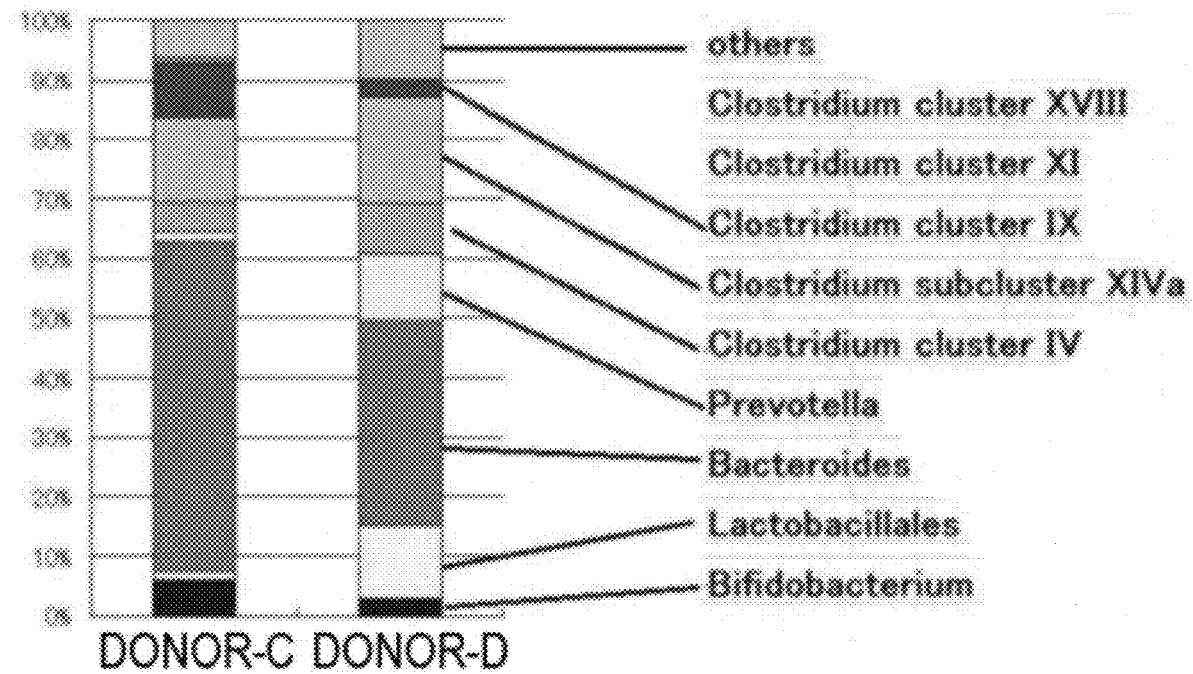
FIG. 11B is a diagram showing a change in the intestinal flora of a "recipient" (patient suffering from chronic fatigue syndrome) when administering a composition of the present invention (intestinal flora derived from "donors"), in which feces were corrected at the times (1)-(5).
Figure 11B:
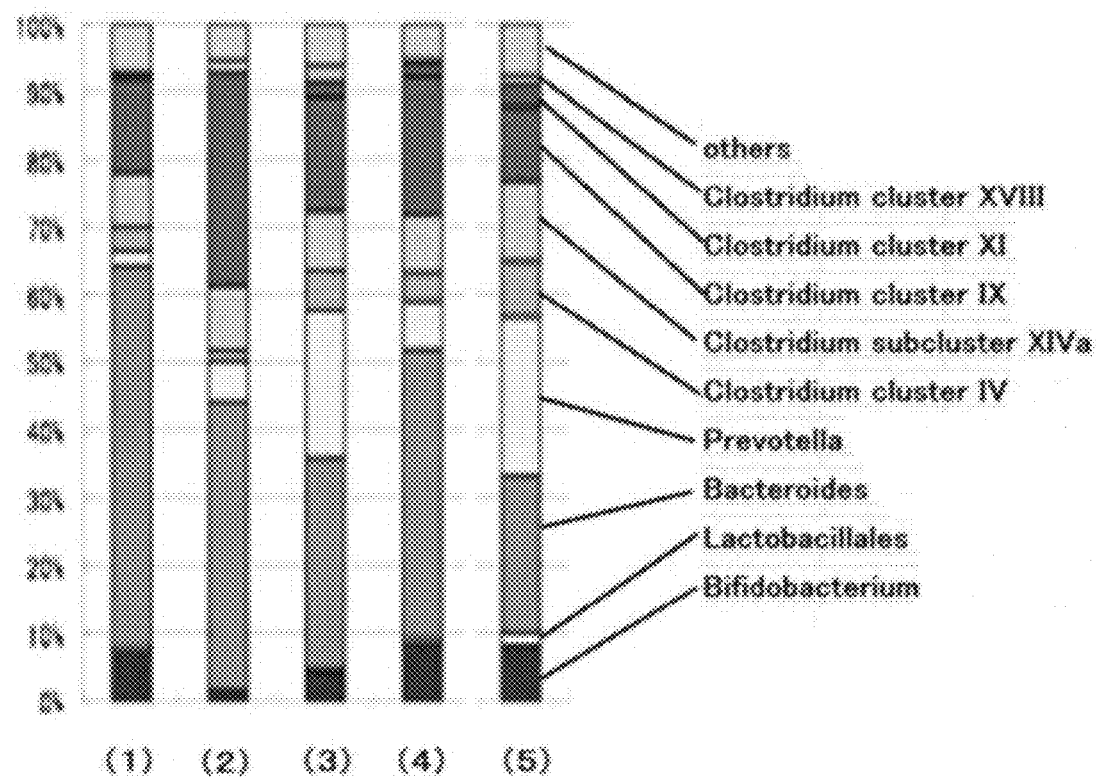

FIG. 11B shows the results from the examination of the intestinal flora balance in feces collected in (1), (2), (3), (4), and (5) above.

Results

As shown in FIG. 11B, *Clostridium* cluster IX significantly increased after the implementation of S1, and the balance was greatly disrupted. It was revealed that, in order to regain balance, there was struggle between the transplanted bacteria and the intestinal bacteria of the subject in order to bring the patient balance with the feces transplanted from the subsequent UB1 onward close to the target balance. It was suggested that the mental state may also temporarily become worse after the implementation of S1, but it was revealed that a substantially good balance was obtained after the UB3, and the mental state was stable.

Discussion

The physical condition rather became worse when the conventional method S1 was implemented first, whereas the physical condition smoothly recovered after the implementation of UB1. Therefore, it is clear that the "compositions containing microorganisms derived from a living body" of the present invention in which the nanobubble water is used are much more useful than the conventional "composition containing microorganisms derived from a living body" obtained by dissolving microorganisms derived from a living body in only a physiological saline solution, and can be used as an "agent for improving a physical constitution and/or physical condition".

Test Example 4: Test to Confirm Effect of Improving Various Diseases

The engraftment confirmation test as described above using the "composition of the present invention" was performed on patients of about 300 or more cases that suffered from the diseases shown in Test Example 1 (FIGS. 2 to 9) and others.

As a result, in a considerable number of the patients, the balance of resident microorganisms improved to a level equal to (or higher than) that shown in FIGS. 2 to 9, and furthermore, improvements in various diseases were also seen. In addition, the "intestinal flora transplantation" was performed in 800 or more cases including cases where the engraftment confirmation test as described above was not performed. In a considerable number of the patients of these cases, an effect of improving the symptoms of diseases, and the like were confirmed.

In particular, the degree of improvement was high in "ulcerative colitis", "irritable bowel syndrome", "Crohn disease", "manic depression", "depression", "atopic dermatitis", "costiveness", and the like, and it is considered from these results that transplantation of the "composition of the present invention" to a living body can be greatly expected as an effective treatment method for those diseases.

Test Example 5: Test to Confirm Engraftment Speed

In the about 300 or more cases described in Test Example 4 on which the engraftment confirmation test was performed, depending on the "attribute and/or environment" of the "recipient", in some cases, an effect of the transplantation was realized through a feeling of warmth and the like about several minutes after the transplantation when the "composition of the present invention" was used. In addition, in many cases, a change in the "intestinal flora balance" was confirmed in feces that was first collected within a period from several hours after the transplantation period had finished to the next day.

It is thought from the results above that, with the "intestinal flora transplantation" in which the composition of the present invention is used, intestinal bacteria more reliably engraft at an amazing speed compared with the conventional "intestinal flora transplantation".

Test Example 6: Test for Usefulness of Assistant Solvent for Introduction into Living Body (Test for Stability of Stored Microorganisms)

It is clear from the above-mentioned test examples that the "composition containing microorganisms derived from a living body" of the present invention in which the "assistant solvent for introduction into a living body" (nanobubble water) of the present invention is used is suitable for introducing organic substances such as microorganisms, and the like into a living body. The following describes a test that was performed to examine the suitability of the "assistant solvent for introduction into a living body" of the present invention as a storage solution for microorganisms.
Test Method: Protocol After "compositions containing intestinal bacteria" of 1) and 2) below were cultured for one week in prepared semi-solid media in test tubes manufactured by Kyokuto Pharmaceutical Industrial Co., Ltd., changes of the media due to proliferation of intestinal bacteria and motility of the bacteria were observed and compared.

1) The "composition containing intestinal bacteria" of the present invention prepared using human feces and the "assistant solvent for introduction into a living body B" (nanobubble water B) of Example B of the present invention in the same manner as in Example 1 (bacterial solution: undiluted).

2) A conventional "composition containing intestinal bacteria" prepared using a physiological saline solution (bacterial solution: undiluted).

Figure 12:
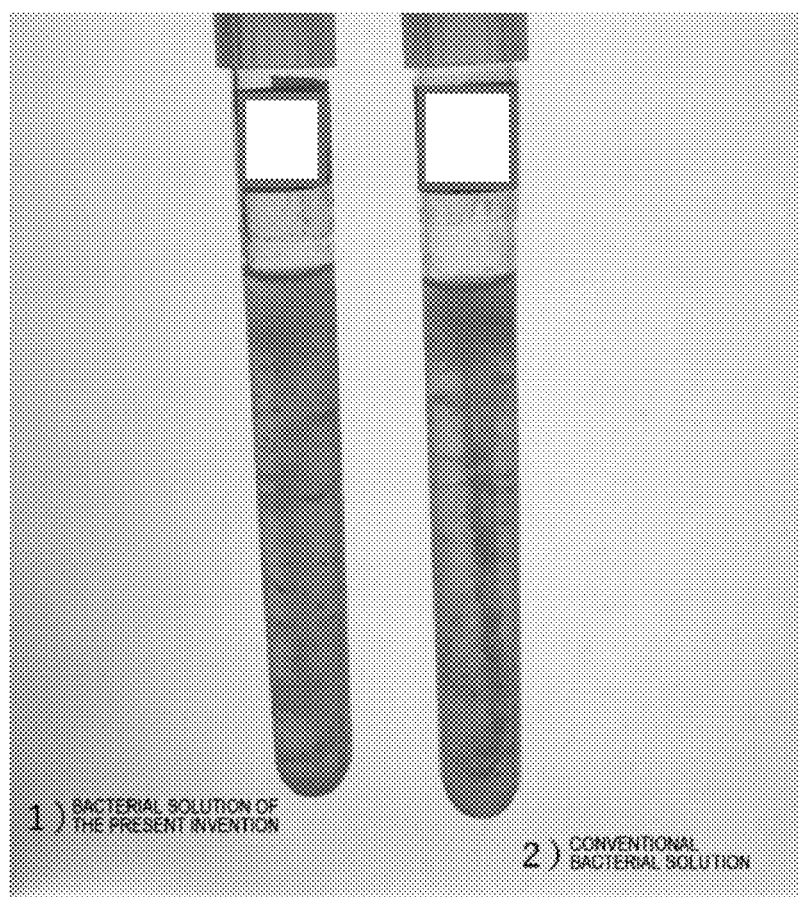
FIG. 12 is a diagram showing the results from a comparison of the stability of microorganisms derived from a living body that are contained and stored in an assistant solvent for introduction into a living body (nanobubble water B) of Example B with the stability of microorganisms derived from a living body that are contained and stored in a physiological saline solution.

A Pasteur pipette was inserted into the above-mentioned medium and used to inject 50 µl of each of the above-mentioned bacterial solutions in the same manner as in a bacterial culture examination. After one week, the appearances were observed and compared. FIG. 12 shows the results.

Results

In the case of the conventional "composition containing intestinal bacteria" of 2), as shown in the right tube in FIG. 12, the "aerobic portion (upper portion of the medium)" and the "portion into which the pipette had been inserted in the anaerobic portion of the deep portion (middle to bottom portion of the medium)" became opaque due to the growth of the bacteria immediately after the insertion, but the color tone of the medium inside the tube excluding those portions did not change from that of the medium itself and was highly transparent even after one week.

That is, the entire intestinal bacterial flora did not seem to be continuously cultured and propagate, and retain biological activity.

On the other hand, in the case of the "composition containing intestinal bacteria" of the present invention of 1), as shown in the left tube in FIG. 12, the "aerobic portion (upper portion of the medium)" and the "portion into which the pipette had been inserted in the anaerobic portion of the deep portion (middle to bottom portion of the medium)" became opaque due to the growth of the bacteria immediately after the insertion, and in addition, the entire medium also became opaque. Thus, the transparency of the entire medium was obviously reduced.

This result shows that the biological activity of the entire intestinal bacteria flora was substantially maintained, that is, the storage stability in the "composition containing intestinal bacteria" (bacterial solution: undiluted) prepared using the "assistant solvent for introduction into a living body" (nanobubble water B) of the present invention remained for a week or longer.

Discussion

The following two ideas are conceivable from the results above.

Firstly, it is simply thought that the "assistant solvent for introduction into a living body" of the present invention is more suitable for storage of microorganisms derived from a living body.

Secondly the results are thought to show that one of the reasons why both the "assistant solvent for introduction into a living body" of the present invention and the "composition containing microorganisms derived from a living body" in which this assistant solvent was used could introduce organic substances such as microorganisms into a living body much more efficiently compared with the prior art in the other test examples and the like is high stability of stored microorganisms derived from a living body.

INDUSTRIAL APPLICABILITY

The "composition of the present invention" can also be administered using a simple method that is less burdensome on a patient compared with a conventional method, and more rapid and more reliable engraftment is achieved irrespective of the administration method and the administration route. Therefore, the "composition of the present invention" is greatly expected to be applied to treatment of various diseases, and the like.

The invention claimed is:

1. A composition containing intestinal bacteria isolated from a human subject, the composition comprising:
   (I) intestinal flora collected from one or more healthy humans or at least one intestinal bacteria isolated from the intestinal flora, wherein the intestinal flora or the intestinal bacteria is always suspended in nanobubble water or immersed in the nanobubble water after the collection;
   and
   (II) nanobubble water including gas bubbles, wherein the gas bubbles consist of one or two gas components selected from air, hydrogen, or carbon dioxide and have an average diameter of smaller than 1,000 nm.

2. A method for manufacturing the composition according to claim 1, comprising at least steps (1) and (2) below:
   (1) producing nanobubble water by generating the gas bubbles in water to obtain (II); and
   (2) dispersing (I) in (II) and suspending the dispersion under stirring, following filtering the dispersion.

3. The manufacturing method according to claim 2, further comprising a step (3) below:
   (3) selecting the intestinal flora or at least one intestinal bacteria selected from the intestinal flora in (I), depending on an attribute and/or environment of an administration target to which the composition is administered.

4. An assistant solvent for promoting colonization of intestinal flora collected from one or more healthy humans or at least one intestinal bacteria isolated from the intestinal flora into an intestinal mucous membrane of a human administration target, comprising (III) below, wherein the intestinal flora or the intestinal bacteria is always suspended in nanobubble water or immersed in the nanobubble water after the collection:
   (III) nanobubble water including an effective amount of nano-sized or smaller gas bubbles for promoting colonization, an average diameter of gas bubbles in the assistant solvent being smaller than 1,000 nm, wherein a gas component consisting of the gas bubbles consisting of one or two gas components selected from air, hydrogen, and carbon dioxide.

5. A method comprising a step of administering the composition according to claim 1 to a human administration target who has at least one disease selected from an inflammatory disease, pulmonary adenocarcinoma, chronic pancreatitis, type 2 diabetes, diabetic dyslipidemia, giardiasis, chronic fatigue, ulcerative colitis, irritable bowel syndrome, Crohn's disease, manic depression, depression, atopic dermatitis, and costiveness.

6. The method according to claim 5, wherein the composition is administered to the human administration target to reconstruct intestinal flora of the human administration target.

7. The method according to claim 5, wherein the composition is administered via an anus of the human administration target.

8. The method according to claim 5, wherein the administration is to promote colonization of intestinal flora contained in the composition or at least one intestinal bacteria isolated from the intestinal flora via an intestinal mucous membrane.

9. The method according to claim 5, wherein the intestinal flora is collected from one or more healthy human or at least one intestinal bacteria isolated from the intestinal flora.

* * * * *